United States Patent
Guzman et al.

(10) Patent No.: US 9,127,529 B2
(45) Date of Patent: Sep. 8, 2015

(54) PROCESS AND SYSTEM FOR PREPARATION OF X-RAY SCANNABLE SAMPLE-EMBEDDED SLIVER FOR CHARACTERIZATION OF ROCK AND OTHER SAMPLES

(71) Applicant: Ingrain, Inc., Houston, TX (US)

(72) Inventors: Bryan Guzman, Houston, TX (US); Naum Derzhi, Houston, TX (US)

(73) Assignee: Ingrain, Inc., Houston, TX (US)

( * ) Notice: Subject to any disclaimer, the term of this patent is extended or adjusted under 35 U.S.C. 154(b) by 141 days.

(21) Appl. No.: 14/061,772

(22) Filed: Oct. 24, 2013

(65) Prior Publication Data
US 2014/0119497 A1   May 1, 2014

Related U.S. Application Data

(60) Provisional application No. 61/721,161, filed on Nov. 1, 2012.

(51) Int. Cl.
| | |
|---|---|
| G01N 23/04 | (2006.01) |
| E21B 49/02 | (2006.01) |
| G01N 23/225 | (2006.01) |
| G01N 1/36 | (2006.01) |
| G01N 33/24 | (2006.01) |

(52) U.S. Cl.
CPC  E21B 49/02 (2013.01); G01N 1/36 (2013.01); G01N 23/046 (2013.01); G01N 23/225 (2013.01); G01N 33/241 (2013.01); G01N 2223/419 (2013.01); G01N 2223/616 (2013.01)

(58) Field of Classification Search
CPC ..... G01N 23/087; G01N 23/12; G01N 23/10; G01N 33/2823
See application file for complete search history.

(56) References Cited

U.S. PATENT DOCUMENTS

| | | | |
|---|---|---|---|
| 4,710,948 A | * | 12/1987 | Withjack ........................ 378/208 |
| 6,516,080 B1 | | 2/2003 | Nur |
| 8,081,796 B2 | | 12/2011 | Derzhi et al. |
| 8,081,802 B2 | | 12/2011 | Dvorkin et al. |
| 8,085,974 B2 | | 12/2011 | Dvorkin et al. |
| 8,155,377 B2 | | 4/2012 | Dvorkin et al. |
| 8,170,799 B2 | | 5/2012 | Dvorkin et al. |
| 8,331,626 B2 | | 12/2012 | Wojcik et al. |
| 8,583,410 B2 | | 11/2013 | Sisk et al. |
| 8,590,382 B2 | | 11/2013 | Zaleski, Jr. et al. |
| 2009/0288880 A1 | | 11/2009 | Wojcik et al. |

(Continued)

OTHER PUBLICATIONS

Sisk, C., et al., "3D Visualization and Classification of Pore Structure and Pore Filling in Gas Shales," Society of Petroleum Engineers Annual Technical Conference and Exhibition, Florence, Italy, SPE 134582, Sep. 19-22, 2010, pp. 1-4.

(Continued)

*Primary Examiner* — Hoon Song
(74) *Attorney, Agent, or Firm* — Kilyk & Bowersox, P.L.L.C.

(57) ABSTRACT

A method is provided to allow characterization of rock or other types of samples using a sliver that is prepared to have a sample and optionally a plurality of thin discrete reference objects encapsulated by hardened encapsulant that surrounds the peripheral edges of the sample and any reference objects. Systems for performing the methods are also provided. An x-ray scannable sliver also is provided as a single unit that has a thin discrete sample and a plurality of thin discrete reference objects encapsulated by hardened encapsulant that encases the peripheral edges of the sample and reference objects.

33 Claims, 10 Drawing Sheets

(56) References Cited

U.S. PATENT DOCUMENTS

| | | |
|---|---|---|
| 2013/0028371 A1 | 1/2013 | Derzhi |
| 2013/0073207 A1 | 3/2013 | Ganz |
| 2013/0094716 A1 | 4/2013 | Carpio et al. |
| 2013/0301794 A1 | 11/2013 | Grader et al. |

OTHER PUBLICATIONS

Curtis, M. E., et al., "Structural Characterization of Gas Shales on the Micro- and Nano-Scales," Canadian Unconventional Resources & International Petroleum Conference, Calgary, Alberta, Canada, CUSG/SPE 137693, Oct. 19-21, 2010, pp. 1-15.

Rosenberg, E., et al., "Microtomography applications in rock analysis and related fields," Computerized Tomography for Industrial Applications and Image Processing in Radiology, Mar. 15-17, 1999, Berlin, Germany, DGZfP-Proceedings BB 67-CD, Paper 2, pp. 9-18, XP-002710056.

Freifeld, B. M., et al., "On-site Geologic Core Analysis Using a Portable X-ray Computed Tomographic System," Lawrence Berkeley National Library, Mar. 1, 2004, (25 pages), XP-002710057.

Coles, M. E., et al., "Applications of CAT Scanning for Oil and Gas Production Research," Mobil Research and Development Corporation, IEEE, 1990, pp. 804-809.

Milner, M., et al., "Imaging Texture and Porosity in Mudstones and Shales: Comparison of Secondary and Ion-Milled Backscatter SEM Methods," Canadian Unconventional Resources & International Petroleum Conference, Calgary, Alberta, Canada, CSUG/SPE 138975, Oct. 19-21, 2010, pp. 1-10.

Wellington, S. L., et al., "X-ray Computerized Tomography,"Journal of Petroleum Technology, Aug. 1987, pp. 885-898.

Gardner, J. S., et al., "Litho-Density Log Interpretation," SPWLA Twenty-First Annual Logging Symposium, Jul. 8-11, 1980, pp. 1-23.

Knackstedt, M. A., et al., "Digital Core Laboratory: Properties of reservoir core derived from 3D images," Society of Petroleum Engineers Asia Pacific Conference on Integrated Modeling for Asset Management, Kuala Lumpur, Malaysia, SPE 87009, Mar. 29-30, 2004, pp. 1-14.

Zhang, S., et al., "The Analysis and Simulation of Rock Properties Using FIB-SEM and Virtual Material Studio," Proceddings of the 2011 NAFEMS World Congress, Mar. 2011, (12 pages), XP-055067172.

Passey, Q. R., et al., "From Oil-Prone Source Rock to Gas-Producing Shale Reservoir—Geologic and Petrophysical Characterization of Unconventional Shale-Gas Reservoirs," Proceedings of the 2010 CPS/SPE International Oil & Gas Conference and Exhibition, Beijing, China, SPE 131350, Jun. 8-10, 2010, pp. 1-29, XP-055067055.

Suhrer, M., et al., "Imaging and Computing the Physical Properties of Gas Shale," Proceedings of the 2010 GeoCanada Conference—Working With the Earth, May 2010, pp. 1-4, XP-055067132.

Communication Relating to the Results of the Partial International Search issued in corresponding International Patent Application No. PCT/US2013/066476 dated Dec. 18, 2013 (4 pages).

Baraka-Lokmane, et al., "Preservation of Core Integrity: A Comparative Study of Core Stablization Products," International Symposium of the Society of Core Analysis, Halifax, Nova Scotia, Canada, Oct. 4-7, 2010, pp. 1-12.

Walls, et al., "Digital Rock Physics Provide Critical Insights to Characterize Eagle Ford," The American Oil & Gas Reporter, Feb. 2011, (4 pages).

Soeder, "Directional Core Analysis of the Mesa Verde Formation, U.S. DOE Multiwell Experiment, Garfield County, Colorado," Institute of Gas Technology, Project No. 61071 Topical Report, Sep. 1984, (66 pages).

International Search Report and Written Opinion issued in corresponding International Patent Application No. PCT/US2013/066476 dated Feb. 25, 2014 (17 pages).

\* cited by examiner

PROCESS AND SYSTEM FOR PREPARATION OF X-RAY SCANNABLE SAMPLE-EMBEDDED SLIVER FOR CHARACTERIZATION OF ROCK AND OTHER SAMPLES

This application claims the benefit under 35 U.S.C. §119(e) of prior U.S. Provisional Patent Application No. 61/721,161, filed Nov. 1, 2012, which is incorporated in its entirety by reference herein.

BACKGROUND OF THE INVENTION

The present invention relates to the field of digital rock physics and, more particularly, to methods of preparing sample-embedded slivers which can be more efficiently and accurately analyzed. The present invention further relates to systems for performing the methods, and an x-ray scannable sliver product which can integrate a sample alone or together with reference objects into a stabilized single unit for handling and x-ray scanning.

Samples of rock obtained from a drilled well have been used to obtain estimates of rock composition and properties such as permeability, porosity, elasticity and other properties, and so forth, which are typical of an entire subterranean rock formation or facies. These estimates can have substantial significance, such as for characterizing the economic value of reservoir rock formations.

One common sample used to estimate rock properties is a well core. Well cores are very small compared to an entire formation, so multiple well cores are typically taken and analyzed and rock properties are interpolated in between geographic locations of the cores. Nevertheless, cores can be approximately a meter in length and $\frac{1}{10}$ meter in diameter. Laboratory analysis of rock samples such as cores can be difficult and time consuming, and typically must be done off-site. Cores must be extracted and shipped to a laboratory for analysis and this can require many days or weeks to complete. Further, physical lab experiments are difficult to perform due to the usual size and shape of well samples such as cores, and the need to use sufficiently large sized samples to obtain accurate results by laboratory analysis.

Devices for generating digital images of rock samples are available for use. These devices include, for example, computer tomographic (CT) devices, scanning electron microscopy (SEM) devices, and FIB-SEM (focused ion beam combined with SEM) devices. Digital rock physics techniques for estimating rock properties have the advantage that they can accurately scan and produce digital images of very fine pore structures and they can identify small volumes of organic materials present in the pore structure of the rock. However, it is very time consuming and expensive to digitally scan very large samples to estimate rock properties. For example, shales can have an average pore size of about 0.005 to 1.0 µm and a well core typically can be about 100,000 µm (0.1 m) in diameter and 1,000,000 µm (1 m) or more in length. Scanning the entire sample at a resolution high enough to identify all of the pores can result in a complete assessment of the pore structure of the sample. However, scanning the entire sample at a resolution high enough to identify all of the pores is not practical due to the time and expense required to do a complete scan.

The present investigators have recognized that if samples of rock are machined down to relatively smaller and thinner dimensions in attempts to overcome the indicated shortcomings of large samples that the physical ability of the smaller sample to tolerate and withstand typical forces associated with machining can be a problem. For example, the present investigators recognized that looser consolidated rock or other types of samples may not be able to physically tolerate machining and other processing and handling used on the sample to prepare it for CT, SEM, or FIB-SEM analysis. The present investigators have further recognized that attempts to stabilize the sample with an integrally attached backing before machining that would still be retained as an attachment at the time of subsequent x-ray projection of the sample can cause interference problems and impair results.

SUMMARY OF THE INVENTION

A feature of the present invention is a method for preparing an unbacked sample-carrier or sliver usable for x-ray scanning, such as x-ray projection imaging and/or computer tomographic (CT) scanning, and evaluation.

A further feature of the present invention is method of providing a sliver having an unbacked sample that is encased around its peripheral edges with an encapsulant, such as a hardened polymer.

Another feature of the present invention is method of providing a sliver having an unbacked sample and reference objects that are encased around their peripheral edges with an encapsulant, such as a hardened polymer.

A further feature of the present invention is a system that includes means for preparing and acquiring an x-ray projection of the indicated unbacked sample-embedded sliver, and means for evaluating scanning results to estimate an outputtable or storable property or compositional characteristic of the sample.

An additional feature of the present invention is an x-ray scannable sliver wherein unbacked sample and reference objects are encased around their peripheral edges with an encapsulant, such as a hardened polymer that stabilizes and facilitates handling of the sample and reference objects as a single unit during further preparation and analysis.

To achieve these and other advantages and in accordance with the purposes of the present invention, as embodied and broadly described herein, a method for preparing a sample-embedded sliver for x-ray scanning and evaluation is provided. The method can include obtaining a cut sample from a plug, such as from a well bore or other subterranean location; encapsulating the cut sample (in an encapsulating material such as a polymer) to encapsulate at least a peripheral edge that extends around the sample and that is located between the opposite sides thereof; exposing (for instance, by machining, grinding, laser, dissolving, and the like), if not exposed already, a flat face of the cut sample to produce a first exposed face; and exposing (for instance, by machining, grinding, laser, dissolving, and the like), if not exposed already, a second exposed face on an opposite side of the cut sample to the first exposed face, wherein the first and second faces are parallel to each other and spaced in part by a thickness of the sample, to provide an energy scannable sliver.

The present invention also relates, in part, to a method for preparing a sample-embedded sliver for x-ray scanning and evaluation which comprises steps of: (i) extracting a plug from a core obtained from drilling a wellbore; (ii) optionally performing a single energy scan on the plug for sample selection; (iii) cutting a selected sample having opposite sides from the plug; (iv) positioning the sample within a casting container; (v) introducing flowable encapsulant, such as a polymer, into the casting container to encapsulate at least a peripheral edge that extends around the sample and between the opposite sides thereof; (vi) hardening the encapsulant (for example, polymer) to form a sample-embedded intermediate carrier which is removable from the container; (vii) machining a side of the sample-embedded intermediate carrier to expose a flat face of the sample to produce a first exposed face; and (viii) machining a second exposed face on an opposite side of the sample to the first exposed face, wherein the first and second faces are parallel to each other and spaced in part by a thickness of the sample, to provide an x-ray scannable discrete sliver comprising a thin planar sample (for instance, a thickness of from about 30 microns to about 5 mm, such as from about 100 microns to 3 mm) encapsulated at a peripheral edge thereof within surrounding encapsulant (e.g., polymer) in thin layer form (for instance, a thickness of from about 30 microns to about 5 mm, such as from about 100 microns to 3 mm) which structurally stabilizes the resulting sliver. The method can further include (ix) capturing at least one digital image of the sliver sample using x-ray scanning.

The present invention also relates to a method for preparing a sample-embedded sliver for x-ray scanning and evaluation which comprises steps of: (i) extracting a plurality of plugs from a core obtained from drilling a wellbore; (ii) machining the plurality of plugs to reduced thicknesses to provide samples; (iii) forming a stack of the samples with spacer slivers positioned between the samples; (iv) performing a multi-energy X-ray CT scan of the stack on a scanning stage at two or more different energy levels with a plurality of reference objects placed around the samples on a scanning stage; (v) creating digital images of the samples from the multi-energy X-ray CT scan, wherein each of the samples scanned at two or more different energy levels returns for each energy a CT value for each voxel thereof; (vi) estimating bulk density, RhoB, and effective atomic number, $Z_{eff}$, per pixel for all the samples based on the digital images of the samples for sample selection; (vii) positioning a selected sample and a plurality of discrete reference objects within a casting container; (viii) introducing flowable encapsulant (e.g., polymer) into the casting container to encapsulate at least a peripheral edge that extends around the sample and between opposite sides thereof, and to encapsulate at least peripheral edges that extend around the reference objects and between opposite sides thereof; (ix) hardening the encapsulant (e.g., polymer) to form a sample and reference object-embedded intermediate carrier which is removable from the container; (x) machining a side of the sample and reference object-embedded intermediate carrier to expose a flat face of the sample and a flat face of each of the reference objects to produce a first exposed side; and (xi) machining a second exposed side on an opposite side of the sample and reference objects to the first exposed side, wherein the first and second sides are parallel to each other and spaced in part by a thickness of the sample and thicknesses of the reference objects, to provide an x-ray scannable discrete sliver comprising a thin planar sample (for instance, a thickness of from about 30 microns to about 5 mm, such as from about 100 microns to 3 mm) and reference objects encapsulated at respective peripheral edges thereof within surrounding encapsulant (e.g. polymer) in thin layer form (for instance, a thickness of from about 30 microns to about 5 mm, such as from about 100 microns to 3 mm) which structurally stabilizes the resulting sliver. The method can further include (xii) capturing at least one digital image of the sliver sample using x-ray scanning.

Systems for performing the methods are also provided.

The present invention also relates to an x-ray scannable sliver wherein a thin discrete sample (for instance, a thickness of from about 30 microns to about 5 mm, such as from about 100 microns to 3 mm) and thin discrete reference objects (for instance, a thickness of from about 30 microns to about 5 mm, such as from about 100 microns to 3 mm) are encapsulated around their periphery edges with encapsulant (e.g., polymer) that can be used to stabilize and facilitate handling of the sample and reference objects as a single unit during further preparation and analysis.

As used herein, a "plug" can be a discrete subsample obtained from a well core, which is not limited to a particular three-dimensional geometrical shape unless otherwise indicated.

As used herein, "x-ray scanning" can refer to two-dimensional x-ray imaging, three-dimensional x-ray imaging, or other x-ray imaging with an x-ray scanning system or device. Non-limiting examples include, for example, x-ray projection imaging, x-ray CT imaging, and the like.

As used herein, "x-ray scannable" materials are materials that can be imaged with use of x-ray scanning.

It is to be understood that both the foregoing general description and the following detailed description are exemplary and explanatory only and are intended to provide a further explanation of the present invention, as claimed.

The accompanying figures, which are incorporated in and constitute a part of this application, illustrate various features of the present invention and, together with the description, serve to explain the principles of the present invention. The features depicted in the figures are not necessarily drawn to scale. Similarly numbered elements in different figures represent similar components unless indicated otherwise.

DETAILED DESCRIPTION OF THE INVENTION

Figure 1:
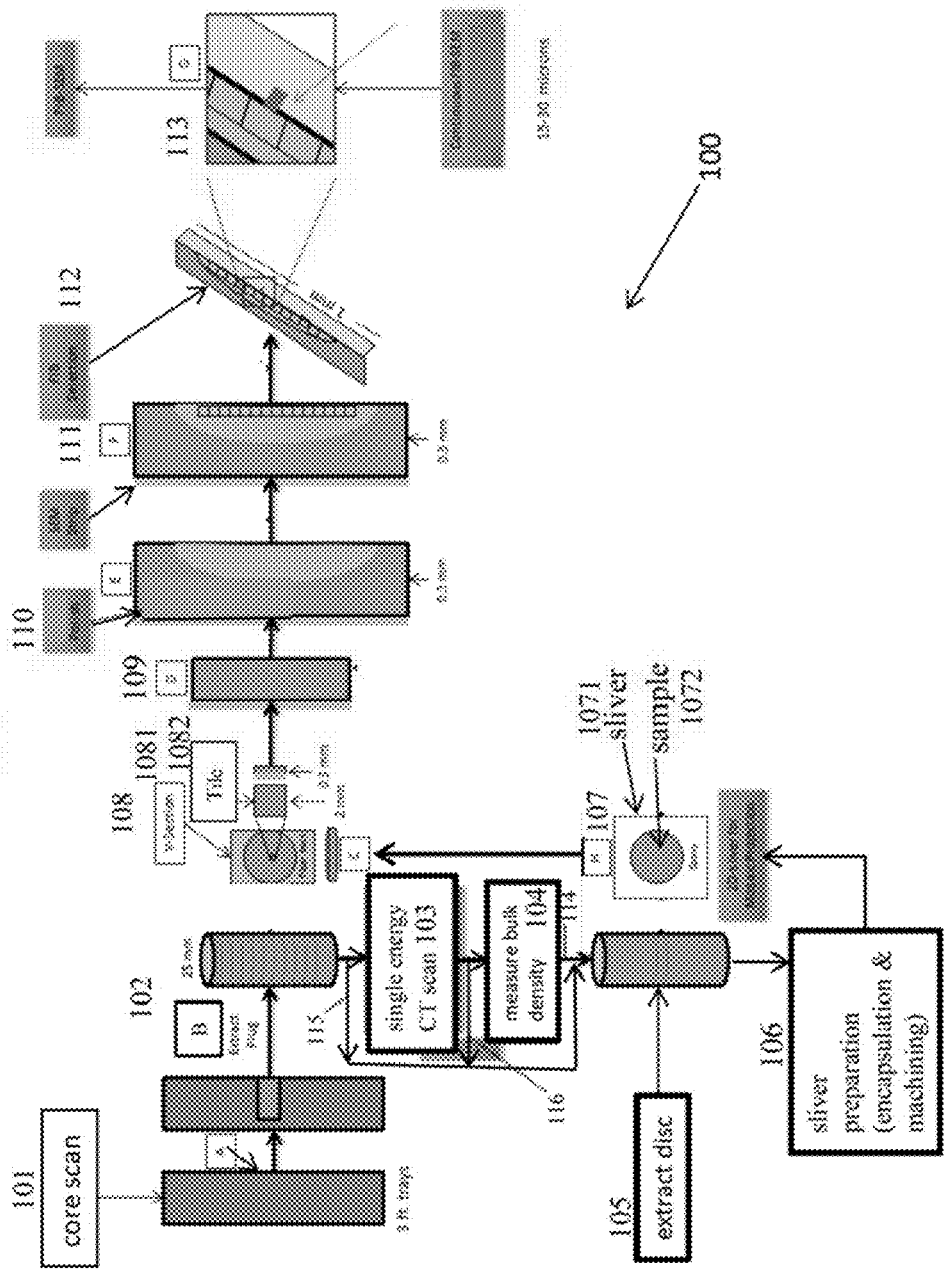
FIG. 1 shows a process flow diagram of the preparation and use of an x-ray scannable sliver that includes a sample in accordance with an example of the present application.

In the present invention, a method for preparing a sample-embedded sliver for x-ray scanning and evaluation is provided. The method can include obtaining a cut sample from a plug, such as from a well bore or other subterranean location; encapsulating the cut sample (in an encapsulating material such as a polymer) to encapsulate at least a peripheral edge that extends around the sample and that is located between the opposite sides thereof; exposing (for instance, by machining, grinding, laser, dissolving, and the like), if not exposed already, a flat face of the cut sample to produce a first exposed face; and exposing (for instance, by machining, grinding, laser, dissolving, and the like), if not exposed already, a second exposed face on an opposite side of the cut sample to the first exposed face, wherein the first and second faces are parallel to each other and spaced in part by a thickness of the sample, to provide an energy scannable sliver.

A method is provided to embed rock or other samples in an encapsulant, such as a polymeric encapsulant or other material, which encases the periphery of unbacked samples to provide a thin unitary sample workpiece or "sliver" (for instance, a thickness of from about 30 microns to about 5 mm, such as from about 100 microns to 3 mm). Other examples of encapsulants include, but are not limited to, glass, a wax, metal, metal oxides, non-polymer compounds. Sliver production according to a method of the present invention facilitates machining (or other thinning techniques) of the samples into thinner and flatter sections without needing to affix them onto a backing of any kind that is carried over into further processing operations and where such a backing, if present, could adversely affect the scanning results. It has been found to be desirable to make sample slivers without backings in order to perform energy scans, such as x-ray projections and/or other x-ray scanning on a rock, without interference from a backing to the rock sample, i.e., another material besides the rock itself For instance, to provide sufficient support for a 30 micron thickness section of rock sample without using the sliver design of the present invention, a glass backing of typically about 1000 microns in thickness may be needed or a carbon fiber backing of about 1000 microns in thickness may be needed to adequately stabilize the sample for processing. For example, the use of the glass backing for thin sample sections involves shaving down the sample after it has been epoxied onto a backing (glass). Machining processes used to cut or grind rock samples can exert considerable physical forces on the rock sample which can damage them. To be useful for providing ample support during machining of the sample, the glass backing typically is not easily removable and typically would be retained and present during subsequent x-ray scanning of the sample for purposes of digital image evaluation. The elimination of the need for such a backing during cutting, grinding, slicing or other machining of thin sections of rock by methods and products of the present invention allows for the accumulation of information about attenuation attributable to the rock sample itself during x-ray projection imaging without interference from a backing. This information can be used for many quantitative techniques for evaluating the composition or a rock property of the sample. The method allows for the collection of x-ray information in a shorter period of time to make this selection than x-ray CT scanning an entire core. For example, the preparation of a sliver in the present methods can incorporate the sample in a machinable and scannable manner without the need of installing a backing on the sample for use at an x-ray projection scanning stage of processing wherein high resolution projections on the sample are performed to produce a patchwork or "mosaic" of two-dimensional (2D) digital images thereof. Another benefit of the method of the present invention is that it allows for better selection of a subsample to be prepared from a rock of interest. The slivers of the present invention can allow for the indicated mosaic of 2D digital images to be produced by the x-ray projection scan, which are more accurate than for backed samples (e.g., glass backed samples). The resulting improved mosaic of 2D digital images that can be obtained with the slivers of the present invention can be useful for selection of a particular sample region of interest of the sample for volumetric and/or even higher resolution analysis (e.g., Higher Resolution Micro CT scanning, SEM, FIB-SEM scanning).

X-ray scannable slivers are also provided in an example of the present invention that can include not only a sample but also reference objects as a unified composite structure. This product is advantageous because reference objects do not have to be separately loaded into the stage of a scanner in which the sliver containing the sample is placed for analysis. The reference objects can accompany the sample in miniaturized form on the same sliver as the sample. The same encapsulant (e.g., encapsulating polymer) can be used to encase the sample and reference objects about their peripheral edges in the sliver. The size of these diverse-object embedded slivers can vary, for example, with sizes provided which are suitable for x-ray projection imaging. These diverse object-embedded slivers can have three-dimensional sizes, for example, such as from about 5 mm to about 100 mm or more (x-direction) by about 5 mm to about 100 mm or more (y-direction) by about 0.1 mm to about 1.5 mm or more (z-direction or thickness) based on Cartesian coordinate axes. More specific examples can include, for example, slivers with dimensions of about 25 mm (x-direction) by about 25 mm (y-direction) by about 0.1 to about 1 mm (z-direction), about 100 mm (x-direction) by about 100 mm (y-direction) by about 0.1 to about 1 mm (z-direction), or other dimensions. In the composite slivers, the sample and reference objects can have sizes that are smaller than the profile or outer edge of the sliver, as they are encased at their peripheral edges within the encapsulant (e.g., polymeric jacket) that also can define the profile of the sliver, and they have thicknesses that are the same or substantially the same as the thickness of the sliver. The sliver thus can be a thin planar rigidized wafer-like composite structure (for instance, a thickness of from about 30 microns to about 5 mm, such as from about 100 microns to 3 mm).

FIG. 1 shows a process workflow including the preparation and use of x-ray scannable slivers in an example of present invention. The process 100 includes a progression of processing stations/steps 101 (A), 102 (B), 103, 104, 105, 106, 107 (H), 108 (C), 109 (D), 110 (E), 111 (F), 112, and 113 (G). The process includes the preparation of an x-ray scannable sliver. In this example, a mosaic of 2D digital images of the sample in the sliver are acquired using x-ray projection scanning, which is used for selection of a smaller sample area of interest that can be tiled and polished for SEM/FIB-SEM analysis.

The process 100 shown in FIG. 1 can begin with a sample, such as a rock sample. A rock sample can be shale, sandstone, or other types of rock or mineral. A well core is an example of one such sample. A well core may have a length of up to about 1 meter or other lengths. In step 101 (A), the well core in this example is scanned at multiple energies (e.g., two, three, four, or more) with an x-ray CT device ("core scan"). The scanning results of the well core, which may be stored and displayable in a log format, can be examined for regions of interest for further evaluation. For example, the results can be examined to determine where bed boundary layers appear to be straight and uniform, and plugs can be extracted from these regions or other regions. For example, from the perspective shown for the core in FIG. 1, such boundary layers can appear as extending horizontally from left-to-right across the core at a right angle or substantially right angle to the major (upright) length shown for the core. These regions can be useful locations for extracting a plug for further evaluation of the rock according to the method of the present invention. For example, in step 102 (B), a plug can be extracted from the core based on the core scanning done in step 101 (A) and the identification of a region of the core where bed boundary layers appear to be straight and uniform. The plug shape can be, for example, a cylindrical shape, such as having a diameter of about 20 mm to about 60 mm, or about 25 mm or other values, and a cylinder length of that can be a greater value than the diameter, such as from about 20 mm to about 125 mm, or other values. As indicated in step 102 (B) in FIG. 1, the plug can be extracted at a right angle (orthogonally) to the major length of the core. This can provide a plug wherein the original boundary layers of the core become oriented in the major length direction of the cylindrical-shaped plug. When a sample disc is extracted from the plug, such as in subsequent step 105 of the process, as a discrete slice removed along the major length of the cylinder, the sample disc that is extracted can be representative of the entire major length of the plug.

Step 103 in FIG. 1 refers to an optional x-ray CT scanning of the plug using a single energy. The results of this single energy scan can be used for selection of a sample section within the plug to be used for further processing in this method. A sample section in the plug containing an area of mineralogical interest can be selected for further processing.

Step 104 in FIG. 1 refers to an optional measurement of bulk density performed on the plug (or disc of step 105) before sliver preparation in step 106. In option 114 of this process flow, the extracted plug is single energy CT scanned and the bulk density of plug (or extracted disc of step 105) is physically measured before diverse sliver preparation in step 106, whereas in option 115 of this process flow, neither of these optional intermediate steps are used, and in option 116 of this process flow, the optional single energy CT scanning step is included but not the optional physical bulk density measurement step.

Bulk density of a plug (or disc) can be physically measured in any suitable manner. One method to do this would be to weigh a plug or group of plugs extracted from the core ($M_1$) and place it/them in a container of known volume ($V_1$). Then the container is filled with water or another liquid and the volume of liquid required to fill the container is recorded ($V_2$). Bulk density ($\rho$) is then calculated, $$\rho = \frac{M_1}{V_1 - V_2}.$$

An entire bulk density of the plug or group of plugs placed in container can be determined in this way.

In step 106, a sliver is prepared with the selected sample, such as the sample disc of step 105. The sample can be stabilized in an encapsulant, for instance, polymer, such as epoxy, and subsequently machined down, such as to approximately 1 mm in thickness or other values, to provide an unbacked sample-embedded sliver available for further processing. In step 107 (H), the sample in this sliver can then have x-ray projection images taken at high resolutions (e.g., ~45 to ~4 microns per pixel) from which a smaller area can be selected for further SEM/FIB-SEM analysis.

As part of sliver preparation step 106, processing is applied to encase the sample disc at its peripheral edge in a hardened encapsulant (e.g., polymer) that can form a thin rigid "jacket" layer (for instance, a thickness of from about 30 microns to about 5 mm, such as from about 100 microns to 3 mm) around the sample disc. This provides a sliver suitable for handling and x-ray projection scanning without the sample needing to be backed at either of its major faces. The stabilization of the sample provided by encasing the sample at its peripheral edge in the encapsulant (e.g., polymer) jacket without need of a sample backing represents a step that can assist in better sample selection for subsequent two-dimensional (2D)/three-dimensional (3D) SEM analysis, such as described herein.

To form such a sample-embedded sliver, the sample can be placed on the bottom of a container, such as a plastic container having a hollow cylinder shape with a mouth opening and a closed bottom. A hardenable encapsulant, for instance, polymer, such as a curable epoxy, can be prepared and poured onto the sample positioned in the container. The inner wall of the container can confine the flow area of the encapsulant (e.g., polymer) when poured or cast onto the sample to define its peripheral shape when hardened. For example, a container can have an inner wall defining a square-shaped opening or other geometry that can be used to define a corresponding shape in the encapsulant (e.g., polymer) material that is poured or cast into the container in forming a stabilization jacket around the sample. The sample can be placed on the bottom of the container, such as centrally located on the bottom or another placement location can be used on the bottom that permits encapsulant (e.g., polymer) to flow around peripheral edges of the sample, when introduced, to encase the sample. For purposes of the present invention, and in any embodiment, the sample can be encased in one or more encapsulants (e.g., polymers). The positioning of the sample within the encapsulant (e.g., polymers) is not important and the sample can be located anywhere in the encapsulant (e.g., polymer(s)) or within the encapsulant (e.g., polymer(s)) (e.g., centered, off-centered, on a side, and the like). The hardenable encapsulant (e.g., polymer) poured into this container with the sample already in position at its bottom can cover the sample at its top surface and flow into an overall shape defined by the cross-sectional shape of the container opening at its bottom and which can have a uniform or substantially uniform thickness, if sufficient encapsulant (e.g., polymer) is introduced. Enough encapsulant (e.g., polymer) is poured to at least cover the peripheral edge of the sample. For a disc shaped sample, for example, the peripheral edge of the sample is the side edge that encircles the disc along the thickness dimension of the disc that connects the two opposite faces of the disc. The encapsulant (e.g., polymer) can be poured over the sample under vacuum or without vacuum. The use of vacuum can be sample dependent. Vacuum, if applied, can draw some of the encapsulant (e.g., polymer) to the lower or bottom side of the sample. The vacuum, if used, preferably is controlled so as not to be strong enough to draw encapsulant (e.g., polymer) into pores of the sample. If a sample is not poured under vacuum, the encapsulant (e.g., polymer) can be allowed to cure for a sufficient time to harden into a rigid material. Once encapsulant (e.g., polymer) is cured, the resulting sample-embedded intermediate carrier can be removed from container. The container optionally can be provided with a non-stick or release coating, e.g., polytetrafluoroethylene (PTFE (Teflon)), if necessary, to assist in removal of the encapsulant (e.g., polymer) and encapsulated sample. If the encapsulant (e.g., polymer) is poured under vacuum, the sample-embedded intermediate carrier can be removed from the container once the material can be handled as a unitary object, and the encapsulant (e.g., polymer) allowed to further cure for a sufficient time to harden into rigid material. For example, an epoxy polymer can be allowed to cure for a designated amount of time specified in the epoxy instructions supplied by the resin vendor. The hardened encapsulant (e.g., polymer) can cover not only the peripheral edges of the sample to which it is attached, but also at least the top surface of the sample. In an example, the container opening is square-shaped, and the sample and container opening have relative sizes that provide a jacket of encapsulant around the periphery of the sample wherein the encapsulant forms a thin layer that outwardly extends from about 1 mm to about 3 mm, or other distances, away from the periphery edge of the sample.

The hardenable encapsulant (e.g., polymer) can be a curable thermosetting resin or a thermoplastic that attaches to the sample upon hardening in direct contact with surfaces and edges of the sample. Curable epoxy resin, can be used as the hardenable encapsulant (e.g., polymer). For example, an epoxy resin which is already flowable can be used, and when it is wanted to cure it, a catalyst is added and mixed that begins a chemical reaction within the epoxy resin that will cause it to cure over the designated cure time for that given epoxy. UV-curable resins can be used. Isocyanate resins can be used. If a thermoplastic is used, the material may be softened with heating to render it sufficiently pourable and flowable, and upon cooling it can harden in place. Once the cast resin is hardened, a cuttings-embedded carrier is formed that can be removed from the casting cylinder and used in further processing according to methods of the present invention.

As further part of the sliver preparation, machining can be used to thin and planarize the sample, and to remove the hardened encapsulant (e.g., polymer) at the face(s) of the sample. This can form a sample-embedded sliver prior to performing x-ray projection scanning on the unbacked sample. For example, machining may be used to reduce the thickness of the sample in the indicated sample-embedded intermediate carrier from a starting thickness of from about 3 mm down to about 1 mm, or other thickness reductions. The hardened encapsulant (e.g., polymer) that encases the sample at its peripheral edges, for example, is thinned by the machining to layer of encapsulant (e.g., polymer) of similar thickness as the sample. The machining can simultaneously thin the sample and encapsulant (e.g., polymer) areas at a similar rate. The encapsulant (e.g., polymer) jacket can be rigid and does not flex out of plane under machining conditions or during subsequent processing. The hardened encapsulant (e.g., polymer) jacket that encases the peripheral edges of the sample stabilizes the sample during these machining operations used to thin and planarize the material. For example, the use of a diamond lap wheel to grind a face of the sample can impart considerable shear stress to the sample. A rock sample, especially a sample not consolidated well, is at risk of being significantly damaged or torn apart during such machining. The rigid encapsulant (e.g., polymeric jacket) stabilizes the sample during machining and can prevent such damage from the machining processes. The encapsulant jacket also provides a standoff region from the sample that can facilitate handling, placement and holding of the sample-embedded intermediate carrier on machining equipment and other process devices.

As an example of how machining can be performed on the indicated sample-embedded intermediate carrier, one side of the sample (as part of the indicated sample-embedded intermediate carrier) can be ground with a lap wheel until a flat face of the rock or other sample is exposed. The sample-embedded intermediate carrier then can be placed on a thin section machine and a new fresh face can be cut on the opposite side of the sample to the fresh face of the rock that was prepared in the previous machining step. It may be difficult to lap both sides of the sample parallel to each other. The lapping of one face of the sample, and cutting of the opposite face can permit the thinning and planarizing to proceed efficiently. The opposite exposed faces preferably are machined to be parallel to each other. In order to lap a side of the sample, a thin section grinder with diamond laps may be used. In order to cut a side of the sample, such as after the opposite side has been lapped as indicated, a thin section machine having a thin section cut-off saw and grinder incorporated into one unit may be used. The sample can be dried, if necessary, before further processing. For example, lap wheels and thin section equipment can introduce a coolant fluid on the workpiece during machining operations, which can be dried off afterwards. The resulting sliver product can be a discrete sliver comprising a thin planar piece of sample as a sliver sample (for instance, a thickness of from about 30 microns to about 5 mm, such as from about 100 microns to 3 mm), which is encapsulated at a peripheral edge thereof within surrounding encapsulant (e.g., polymer) in thin layer form (for instance, a thickness of from about 30 microns to about 5 mm, such as from about 100 microns to 3 mm) which structurally stabilizes the resulting sliver.

The resulting sliver product of these encapsulating and machining steps can be an overall square-profiled sliver including a sample that is encased at its peripheral edges in a encapsulant (e.g., polymer) jacket, such as illustrated in step 107 (H) of FIG. 1. In the top view perspective of the sliver (1071) shown in step 107 (H), the sample (1072) is shown as the disc-shaped heavier-shaded object that is located within a square-profiled unshaded area that represents an epoxy jacket structure that encases the sample. The sample is not limited to a circular profile (or overall disc shaped body), and the encapsulant (e.g., polymer) jacket is not limited to a square profile, as these profiles or shapes are shown here for sake of illustration only. For example, the sample may have a rectangular shape (e.g., square), and the encapsulant (e.g., polymer) jacket may have a circular, square, or non-squared rectangular shape, or other shapes and combinations of shapes may be used. Other encapsulant (e.g., polymer) jacket shapes can provide the indicated sample stabilization for machining and other handling and processing.

Following the preparation of the sliver in step 106, in step 107 (H) sample x-ray projection scanning can be performed and used for selection of an area that can be prepared for 2D SEM or FIB-SEM analysis. For example, the sliver can be placed in a high resolution x-ray projection scanner for at least one x-ray projection image to be acquired. At higher scanning resolutions, it may not be possible to digitally image the entire face of the sample. A plurality of 2D digital images can be obtained across the face of the sample in the sliver using x-ray projection scanning at higher resolution to generate a mosaic of the images that can be digitally stitched together. Depending on the resolution used and sample size, 11×11 images, or 6×6 images, or 6×7 images, or other grids of images can be captured across the face of the sample and stitched together via computer to construct an image of the whole face of the sample. This mosaic image can be used for improved sample selection using x-ray attenuation as the variable from which interpretations are made. A sample area of interest can be selected from the mosaic image for evaluation in even higher resolution analysis using SEM and FIB-SEM. For example, depending on the interest, porosity, calcite presence, or other factors can be used in selecting a sample area of interest.

Referring to step/station 108 (C) in FIG. 1, the sliver having the embedded sample that includes the selected area in step 107 (H) is mounted on a backing layer, such as a carbon fiber backing layer, for support. This intermediate workpiece is indicated at "V-section" 1081 in FIG. 1. A tile, such as square-shaped tile, which includes the selected area in previous step 107 (H) and the portion of backing layer directly behind that region is cut out for use in SEM/FIB-SEM analyses. This workpiece is indicated as "Tile" 1082 in FIG. 1. The backing layer may have a thickness of from about 1 mm to about 1.1 mm, or other values. The sliver can be bonded to the backing layer using an adhesive, such as an epoxy. The epoxy can be, for example, an epoxy resin which is already flowable, and when it is desired to initiate curing of the resin, a catalyst can be added and mixed that begins a chemical reaction within the epoxy resin that causes it to cure over a designated cure time for that given epoxy. For example, a two part epoxy coating kit may be used having these features. The adhesive cure time may be at least partly controllable by temperature conditions. The adhesive can be applied in a very thin substantially continuous coating to at least one of the backing layer and sample, and the two components can be pressed into contact at the adhesive-coated surface(s) and left or held in position until the intervening adhesive cures and hardens to attach them together. After the sliver is attached to the backing layer, the selected area can be extracted as a discrete tile that includes the portion of the backing layer that is located behind the selected area. A tile can be cut from the sliver/attached backing layer, such as with a diamond band saw or other suitable high precision cutting device. For example, a water-cooled, thin bladed diamond band saw may be used to cut out the tile.

Optionally, after step 107 (H) and before the sliver is mounted on the backing in step 108 (C) and the indicated tile extracted, elemental analysis can be performed for the indicated selected area of step 107 (H) and across the face of the sample in the sliver, such as by x-ray fluorescence microscopy (XRF)(not shown). This can be used for additional mineralogical analysis of the sample, if desired.

At stage 109 (D) of the process, the extracted tile may include the selected sample area in a 3D size of about 1 mm to about 10 mm (x-direction) by about 1 mm to about 10 mm (y-direction) by about 0.1 to about 2 mm (z-direction or thickness), or about 1 mm to about 3 mm (x-direction) by about 1 mm to about 3 mm (y-direction) by about 0.1 to about 1 mm (z-direction), or other dimensions suitable for the analyses. For example, the extracted tile may include the selected sample area with a 3D size of about 2 mm (x-direction) by about 2 mm (y-direction) as lateral side length dimensions by about 0.3 mm (z-direction or thickness). These values are merely illustrative, and other values may be used.

In step 110 (E), the extracted tile can be mounted to a blade in order to polish a surface of the exposed rock using a polisher. In step 110 (E) in FIG. 1, the area to be polished is indicated by the lighter shaded region along the right-hand side of the rock sample. For example, after being cut, tiled samples can be optionally mechanically polished and a final ion beam polishing can be performed using an ion polisher. The surface of the tiles preferably can be sufficiently smooth such that a clear image can be produced from a scanning electron microscope (SEM).

In step 111 (F), SEM scanning of the polished area of the sample can be performed. The areas within the indicated boxes represent separate 2D SEM FOV images that are to be segmented to compute a rock property, for example, porosity, TOC (total organic content), and porosity associated with TOC. In step 113 (G), a representation of a 3D FIB-SEM (Focused Ion Beam SEM) location is shown along the top of the polish. This area can be selected in step 112, for example, based on the 2D SEM FOV images. FIB-SEM acquisition can be performed and a 3D high resolution volume can be collected. Segmentation and computations can be performed on this volume to give porosity, TOC, porosity associated with TOC, permeability, and so forth. The adaption and application of SEM and FIB-SEM scanning methods and equipment to tiles of the present invention, as well as the segmentation and rock property calculations can be performed, for example, in manners within the skills of persons knowledgeable in field of digital rock physics.

Optionally, after the SEM analysis of step 111 (F) and before the FIB-SEM analysis of step 113 (G), the sample can be analyzed by energy dispersive spectral analysis (EDS)(not shown). EDS capability can be used to make 2D scans, for example, at nominally 20 nanometer resolution. EDS is an analytical technique used for the elemental analysis or chemical characterization of a sample. The EDS spectrum can comprise estimates of rock materials, such as clay, pores, organic matter, calcite, quartz, plagioclase, pyrite, titanium dioxide, and estimates of similar materials and combinations thereof. The SEM image with EDS can be used to identify the pores, mineralogy and organic content of the sample. In FIGS. 1, 4, 6, 7, and 8, numerical values for some workpiece dimensions are indicated at several steps of the processes for sake of illustration only, and other values may be used.

Figure 2:
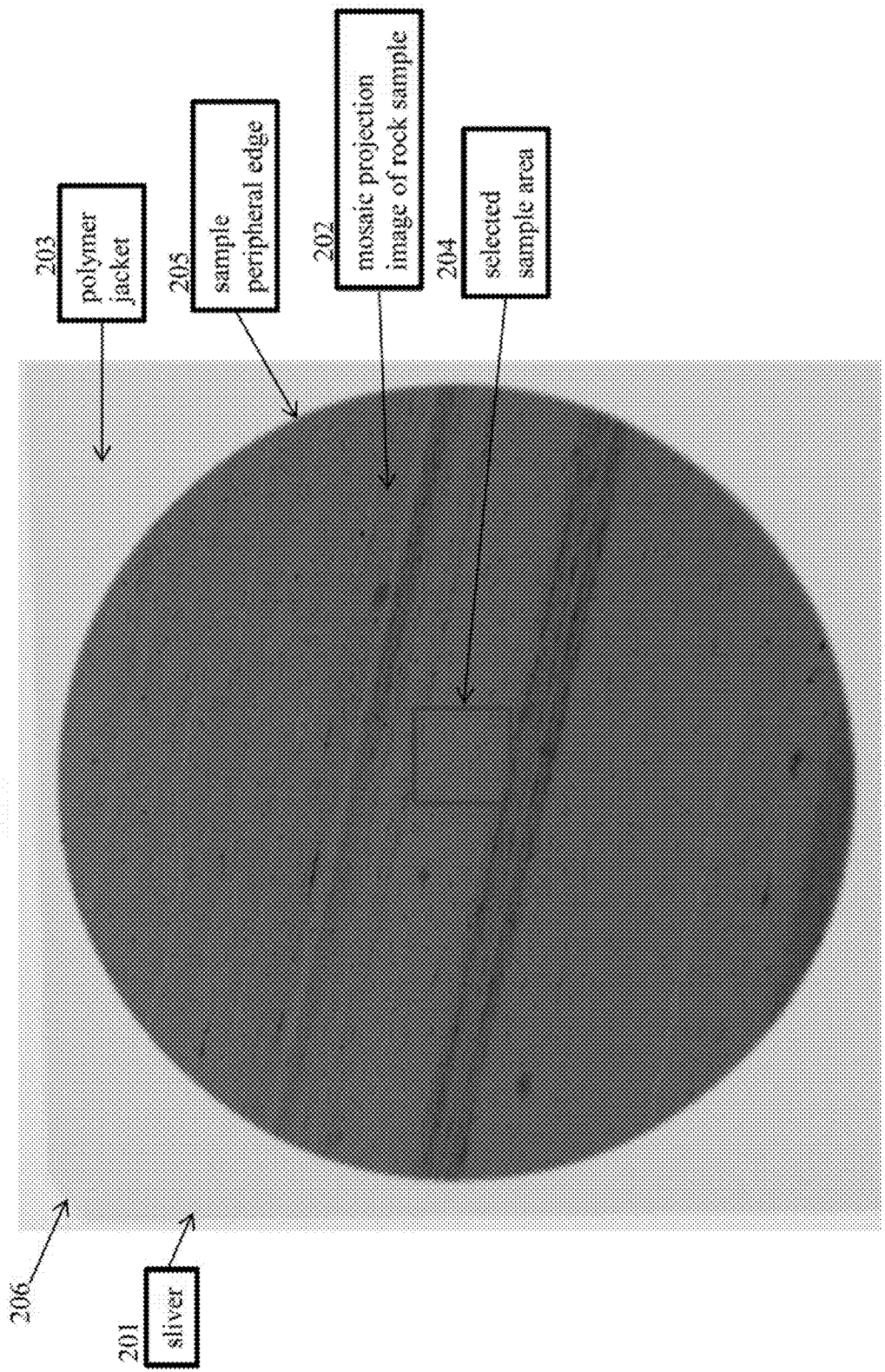
FIG. 2 is an enlarged x-ray projection image of a sample in a sliver according to an example of the present application.

FIG. 2 is an example of enlarged mosaic image of a sample 202 generated from x-ray projection imaging of a sample in a sliver 201 of an example of the present invention, such as prepared in step 106 and shown in step 107 (H) in FIG. 1. The rectangle in FIG. 2 indicates a smaller area 204 of the sample that has been selected for further evaluation (e.g., for further processing in steps 108-113 in FIG. 1), such as based on qualitative evaluation of the mosaic image. As also shown in FIG. 2, the sample has a peripheral edge 205 that is encased by the encapsulant (e.g., polymer) jacket 203. The upper left-hand corner 206 of the encapsulant (e.g., polymer) jacket 203 is shown in this example to be chamfered, which may be provided to facilitate placement of the sliver 201 in a machining device and the like, but is not a required feature of the sliver.

Figure 3:
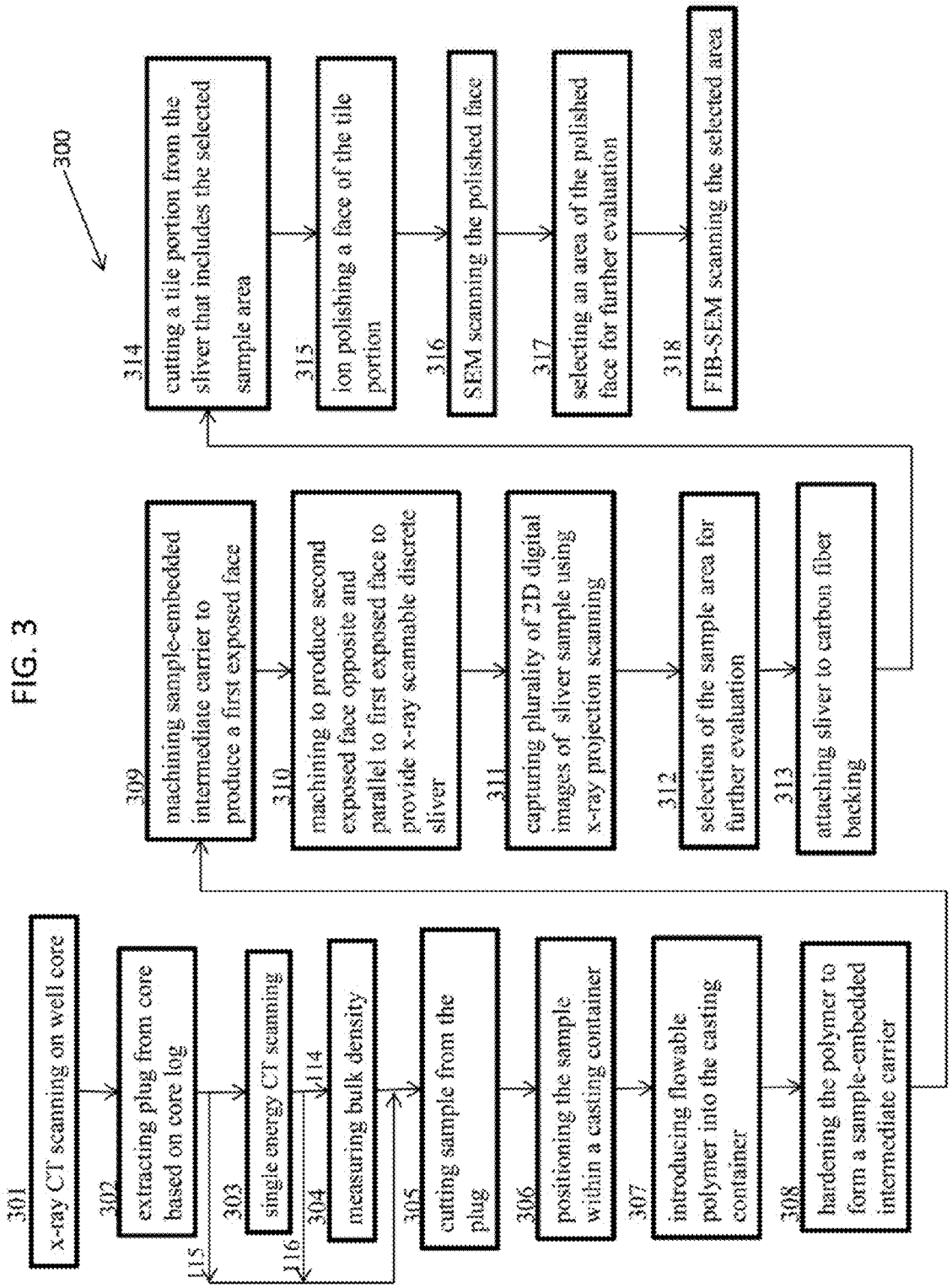
FIG. 3 shows a flow chart describing a method according to an example of the present application.

FIG. 3 shows a method 300 that includes steps 301-318 that can be used in an example of a method of the present invention. This method can be applied, for example, to the workflow shown in FIG. 1. Options 114, 115 and 116 shown in FIG. 3 are the same options as indicated for FIG. 1.

Figure 4:
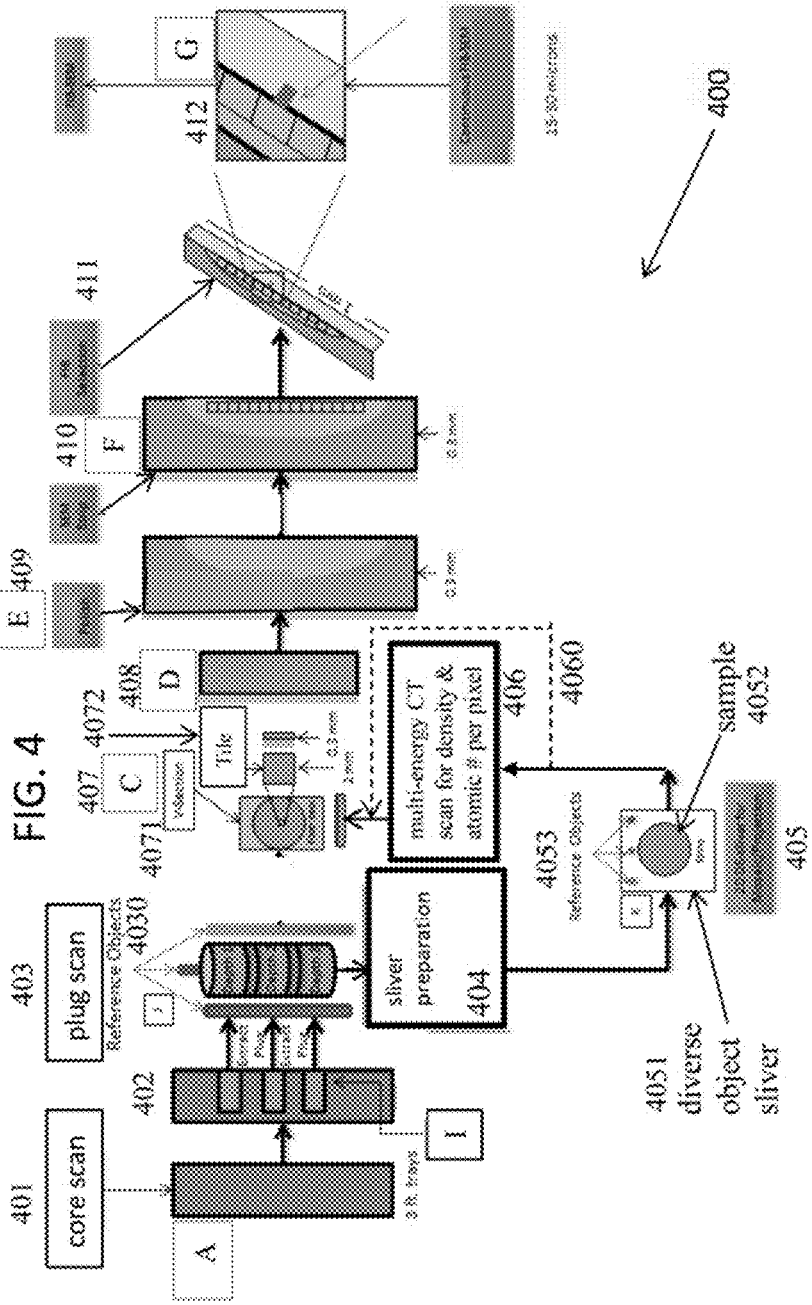
FIG. 4 shows a process flow diagram of the preparation and use of an x-ray scannable sliver that includes a sample and reference objects in accordance with an example of the present application.

FIG. 4 shows a process workflow including the preparation and use of x-ray scannable diverse object-embedded slivers in another example of present invention. These slivers also may be referred to herein as "diverse object slivers." In this example, a single sample along with two, three or more reference objects can be stabilized in the same mass of encapsulant (e.g., polymer) and subsequently machined down to a reduced thickness (e.g., to approximately 0.1 to 2 mm or from 0.1 to 1 mm in thickness). This sample can then have x-ray projection images taken at high resolutions (e.g., ~45 to ~4 microns per pixel, or other resolutions), such as for use in selection of a smaller area or region of the sample for tiling and SEM/FIB-SEM analysis. Using the reference objects that are incorporated into the same sliver as the sample with scanning of the sliver at multiple energies, the density and atomic number of the sample also can be computed per pixel. This information can further assist the selection of a sample area for further analysis.

In further detail, the process 400 in FIG. 4 includes a progression of processing stations/steps 401 (A), 402 (I), 403 (J), 404, 405 (K), 406, 407 (C), 408 (D), 409 (E), 410 (F), 411, and 412 (G). The process includes in part the preparation of an x-ray scannable diverse object-embedded sliver which further includes reference objects integrally in the sliver in addition to the sample. In this example, a mosaic of 2D digital images of the sample in the sliver also are acquired using x-ray projection imaging, which is used (at least in part) in the selection of a smaller sample area of interest that is tiled for SEM/FIB-SEM analysis. Different from the process flow 100 of FIG. 1 wherein bulk density can be measured manually for the samples (discs, plugs), in the process 400 shown in FIG. 4 the bulk density and atomic number can be computed for all samples prior to sliver preparation using one of the samples with reference to results of multi-energy x-ray CT scanning using reference objects external to the samples, and the density and atomic number of the selected sample used in the diverse-object embedded sliver can be computed per pixel with reference made in part to the reference objects integrally included in the same sliver with reference to results of additional multi-energy x-ray CT scanning that can be incorporated into the process flow. As indicated, the x-ray scannable sliver that includes not only the sample but also reference objects is a product that is advantageous because reference objects do not have to be separately loaded into the stage of an x-ray scanner in which the sample sliver is placed for analysis. The reference objects can accompany the sample in miniaturized form on the same sliver as the sample, and the same encapsulating encapsulant (e.g., polymer) can be used to encase the sample and reference objects about their peripheral edges in the sliver, and the different materials can be simultaneously machined to a planarized reduced thickness.

The process 400 shown in FIG. 4, as with the process of FIG. 1, can begin with a sample, such as rock sample. As indicated, the rock sample can be shale, sandstone, or other types of rock. A well core, such as indicated, can be used as the source of the sample. Similar to step 101 shown for the process of FIG. 1, in step 401 (A), the well core in this example is scanned at multiple energies (e.g., two, three, four, or more) with an x-ray CT device ("core scan"). The scanning results of the well core may be stored and displayable in a log format. The scan results can be examined for regions of interest for further evaluation, such as to determine where bed boundary layers appear to be straight and uniform. Regions where boundary layers extend across the core such as shown in FIG. 4 at a right angle or substantially right angle to the major (upright) length shown for the core can be useful locations for extracting a plurality of plugs for further evaluation of the rock according to this method of the present invention. For example, after the indicated core scan, a plug can be extracted from the core where bed boundary layers are straight and uniform. In this method, multiple selections of plugs for extraction at differing depths along the side of the whole core are made and those plugs are extracted for further analysis. In step 402 (I), a plurality of plugs, such as three plugs in the illustration, are extracted from the core based on the DE scanning done in step 401 and the identifications of regions of the core where bed boundary layers appear to be straight and uniform. The shape and dimensions of the extracted plugs can be similar to that described for the process of FIG. 1. Similar as described for plug extraction step 102 (B) in FIG. 1, the plugs in step 402 (I) can be extracted at right angles (orthogonally) to the major length of the core. As indicated, this can provide plugs wherein the original boundary layers of the core become oriented in the major length direction of the cylindrical-shaped plugs.

In step 403 (J)("plug scan"), the extracted plugs are machined down to samples that have a thickness of from about 4 to about 6 mm, or other values, and are stacked for placement and analysis within a dual energy microstage of a multi-energy x-ray CT scanner (e.g., a dual energy x-ray CT scanner). In forming the stack, 2, 3, 4, or 5 or more plugs can be machined into individual samples that are used in forming the stack. The samples are separated by thin slivers of an object that can have near equal density and atomic number (e.g., glass, epoxy) to the samples. In FIG. 4, three samples obtained from three different depth intervals of the core are shown for illustration (i.e., samples "Depth 1," Depth 2," and "Depth 3"). Two spacers 412 are shown in FIG. 4 as individually placed between respective pairs of the three samples. Other numbers of samples and spacers may be used. The spacers can be, for example, glass discs or epoxy discs that have a thickness of about 1 mm to about 2 mm or other values. For example, the spacers, such as glass or epoxy spacers, can be denser than air but have a bulk density less than about 1.6 g/cm$^3$. The samples and spacers can have a diameter, for example, of about 10 mm to about 40 mm, or about 25 mm or other values. The samples and spacers can have the same or substantially the same diameter to provide a stack that can be easier to handle and analyze. In an example, a 3D dual energy x-ray scan can be performed on up to 5 samples from different plugs placed within one field of view (FOV) of the scanner wherein the sample are separated by glass slivers. To assist in estimating the bulk density, atomic number, or both, of the samples in the stack, two, three or more reference objects (4030) external to the samples can be placed around the stack of samples on a microstage of a multi-energy X-ray CT scanner, such as a dual energy x-ray CT scanner. The reference objects can be used, for example, in computing both density and atomic number at a high resolution for all samples within the indicated apparatus. The general steps in the method of analysis include, but are not limited to, 1) performing a scan (such as a dual energy x-ray CT scan) of the target object and reference objects, and 2) calculating density and effective atomic number for the target object, based on the high and low energy CT values. This method of analysis can be performed as an application of the descriptions of U.S. patent application Ser. No. 13/890,367 (Grader et al.), and U.S. patent application Ser. No. 13/527,660, filed Jun. 20, 2012, published as U.S. Patent Application Publication No. 2013/0028371 A1, which are incorporated in their entirety by reference herein. With regard to the three or more reference objects, these objects can be liquid or solid materials such as polymers, metals, minerals or chemical compounds. Each of the reference objects can have a different effective atomic number and/or bulk density from each of the other reference objects. The reference objects are generally homogeneous and made of materials with known and different densities and effective atomic numbers. The density and atomic number values of the reference objects should cover the expected range of densities and atomic numbers in the target object under investigation. The reference objects can be, for example, polymer, mineral, glass, ceramic, water, amber, wood, or other materials. Liquids like water, if used, as a reference object, can be contained in a glass tube. This evaluation of step 403 has been illustrated for a stack of plugs, and it also may be performed on a single extracted plug, wherein no spacer need be used.

After scanning the stack of samples in step 403, an x-ray scannable diverse object-embedded sliver is prepared in step 404. In step 405 (K), the sample in the diverse object sliver is x-ray projection scanned to generate a mosaic image that can be used for sample selection for tile preparation. As an initial part of sliver preparation step 404, processing is applied to encase a selected one of the samples from step 403 at its peripheral edge in a hardened encapsulant (e.g., polymer), and also encase at least two, three or more references objects at their respective peripheral edges in the same hardened encapsulant (e.g., polymer), to form a thin rigid "jacket" layer (for instance, a thickness of from about 30 microns to about 5 mm, such as from about 100 microns to 3 mm) around the sample and reference objects. This can provide a diverse object sliver suitable for handling, and x-ray projection imaging and/or multi-energy x-ray projection scanning, without the sample needing to be backed at either of its major faces. The reference objects that can be incorporated into the sliver with a sample preferably comprise of two, three or more reference objects which have a different bulk density and/or effective atomic number from the sample included in the same sliver and each other. The reference objects can be, for example, polymer, mineral, glass, ceramic, water, amber, wood, or other materials. Liquids like water, if used, as a reference object, can be contained in a glass tube. The reference objects used can be, for example, quartz, polytetrafluoroethylene (PTFE (Teflon)), and amber, and optionally additional different materials. The reference objects preferably can be diverse materials that have known respective bulk densities and effective atomic numbers, which can be effectively and conveniently used as reference or calibration materials for estimating the bulk density and effective atomic number of the sample included in the same sliver based on simultaneous multi-energy x-ray projection scanning performed on the sliver. Further, in an example, this determination can be accomplished wherein the sample of the sliver is free of a backing. As indicated, backings are undesired during such scanning as they can cause interference.

To form such a sample and reference object-embedded sliver, such as indicated in step 404 in FIG. 4, the sample and reference objects can be placed in spaced apart locations at the bottom of the indicated casting container. A hardenable encapsulant (e.g., polymer), such as a curable epoxy, can be prepared and poured onto the sample and the references objects placed in the container. Enough encapsulant (e.g., polymer) is added to encase the peripheral edges of the sample and the reference objects, and surplus encapsulant (e.g., polymer) can cover the top surface of the samples and reference objects, and optionally also their bottoms depending on whether a vacuum is applied during the encapsulation process. The choice of type of encapsulant (e.g., polymer), use of vacuum, and manner of cure, and so forth, can be selected based on similar considerations as described herein for step 106 of the method shown in FIG. 1. Once the encapsulant (e.g., polymer) is cured, the sample and reference object-embedded intermediate carrier that is produced is removed from the container for further processing. The encapsulation can be performed similar to what was described for step 106 of FIG. 1, but with the additional encapsulation of the reference objects as well as the sample in this method.

The sample and reference object-embedded intermediate carrier can be reduced in thickness and planarized at both sides or faces into parallel opposite surfaces by machining. The machining described herein for the sliver that contained the sample without reference objects also can be used on the sample and reference object-embedded intermediate carrier to form a sliver. For example, the sample and reference objects in the intermediate carrier can be lapped on one side, and cut on the opposite side adequate to expose faces of the samples and reference objects at opposite parallel sides of the resulting sliver. The samples and reference objects can be consolidated into a sliver in this method with exposed opposite faces thereof and without any backings. Interference errors that can be caused from the presence of sample backings during x-ray scanning of the sliver can be avoided. The machining may be used to reduce the thickness of the sample and reference objects in the sample and reference object-embedded intermediate carrier from a starting thickness or thicknesses ranging from about 2 mm to about 10 mm, or other values, down to about 1 mm, or other reductions. As can be appreciated, even if the sample has an initial thickness of about 5 mm before machining, for example, the diverse reference objects also may have diverse starting thicknesses relative to the sample and each other. The machining operations can impart uniform thicknesses in the sample and all of the reference objects while also exposing and planarizing their opposite faces so that the sliver can be scanned more easily and accurately. The hardened encapsulant (e.g., polymer) that encases the sample at its peripheral edges, for example, also is thinned by the machining to a layer of encapsulant (e.g., polymer) of similar thickness as the sample and reference objects.

In step 405 (K), x-ray projection imaging of the sliver (4051) containing the sample (4052) and reference objects (4053) is performed to generate a mosaic image in this example that can be used in the selection of an area that can be prepared for 2D SEM or FIB-SEM analysis. For example, the sliver can be placed in a high resolution x-ray projection scanner for at least one x-ray projection image to be acquired. At higher scanning resolutions, as indicated, it may not be possible to digitally image the entire face of the sample. A plurality of 2D digital images can be obtained across the face of the sample in the sliver using the x-ray projection scanning at higher resolution to generate a mosaic of the images that can be digitally stitched together. This mosaic image can be used for improved sample selection using x-ray attenuation as the variable from which interpretations are made. A sample area of interest can be selected from the mosaic image for evaluation in even higher resolution analysis using SEM and FIB-SEM.

In addition to the scanning of the sliver for the x-ray projection image in step 405, the sliver optionally can be scanned at multiple energies in a high resolution x-ray CT scanner to so that both density and atomic number can be computed per pixel for the sample. This is illustrated as step 406 in FIG. 4. In conjunction with the reference objects embedded together with the sample in the same sliver, this image can be processed and density and atomic number can be produced for the sample which can be used to improve sample selection for processes such as segmentation, computations, and various other quantitative measurements. This method of scanning at multiple energies to produce both density and atomic number per pixel can be performed as an adaption of the descriptions of the incorporated U.S. patent application Ser. No. 13/890, 367 (Grader et al.), and U.S. Patent Application Publication No. 2013/0028371.

After step 405 (K) of the process flow shown in FIG. 4, and optional step 406 may be used, and steps 407 (C), 408 (D), 409 (E), 410 (F), 411 ("FIB Selection"), and 412 (G) can be used on the selected sample area for tile preparation, polishing, and SEM and FIB-SEM analysis such as similar to steps 108 (C), 109 (D), 110 (E), 111 (F), 112, and 113 (G), respectively, of the process flow 100 shown and described herein for FIG. 1. Process pathway option 4060 indicates that step 406 is not included between steps 405 and 407 in an option of the method. "V-section" 4071 and "Tile" 4072 can be similar to V-section 1081 and Tile 1082, respectively, in FIG. 1.

Figure 5:
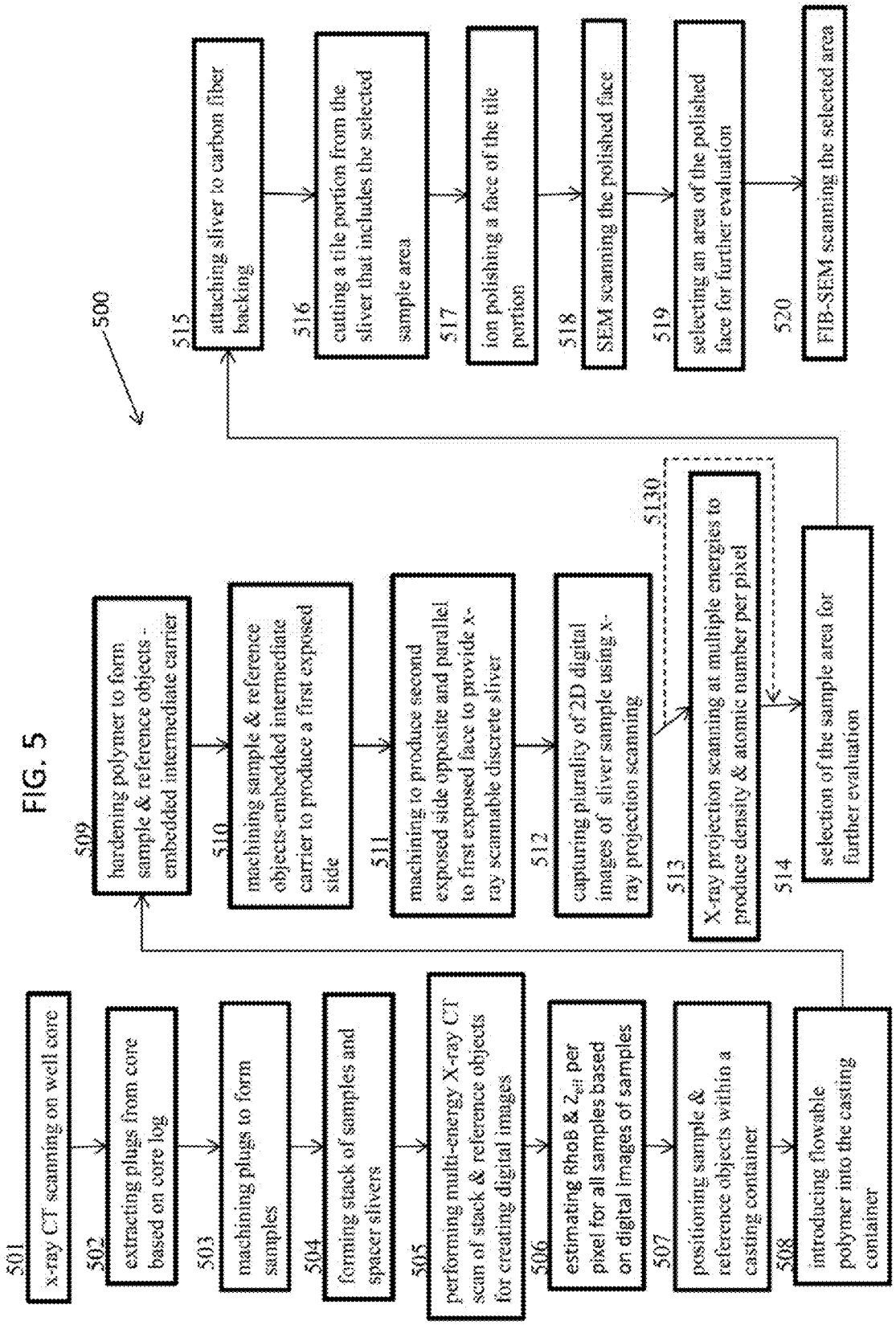
FIG. 5 shows a flow chart describing a method according to an example of the present application.

FIG. 5 shows a method 500 that includes steps 501-520 that can be used in an example of a method of the present invention. This method can be applied, for example, to the workflow shown in FIG. 4. Process pathway option 5130 indicates that step 513 is not included between steps 512 and 514 in an option of the method.

Figure 6:
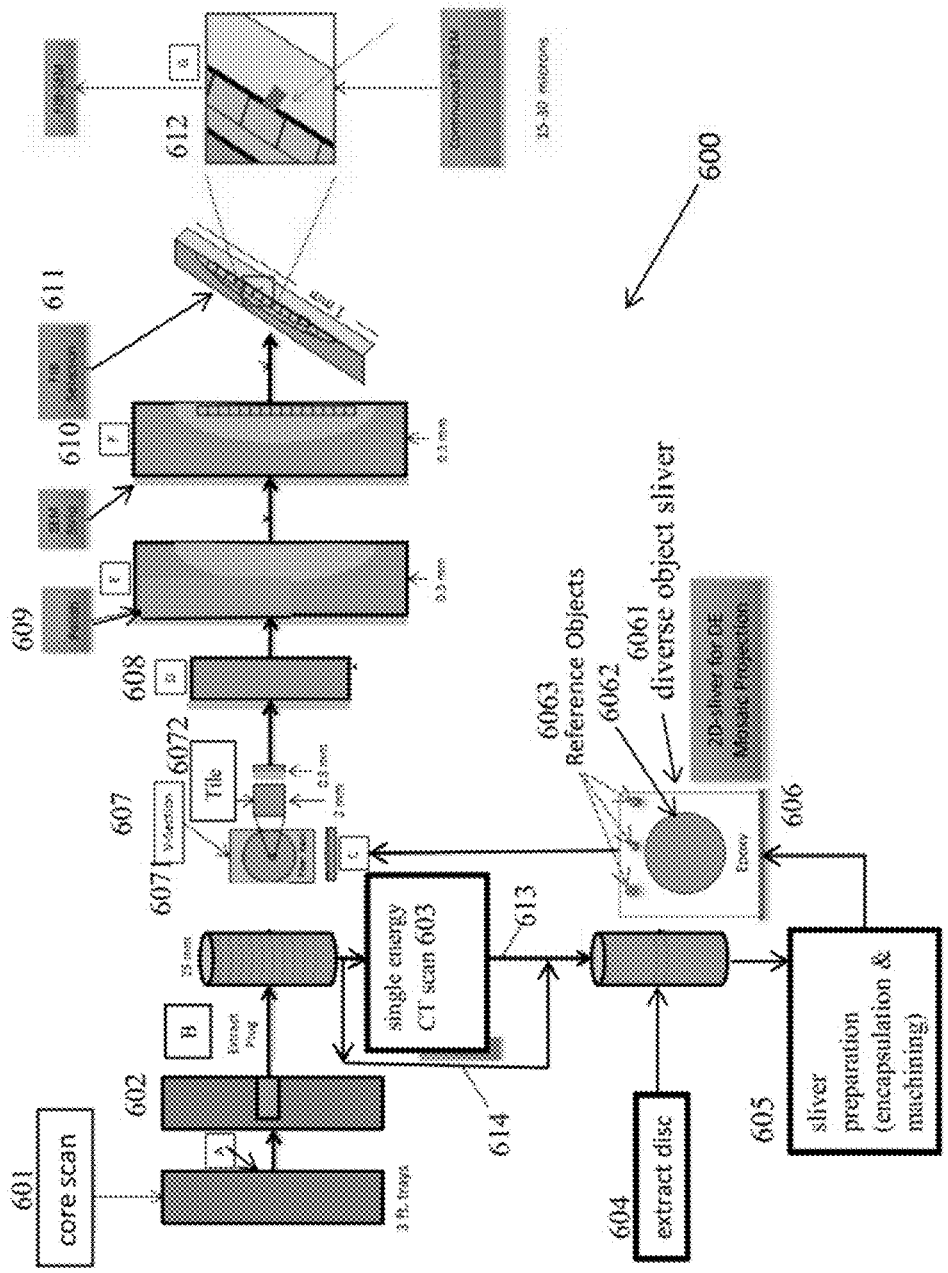
FIG. 6 shows a process flow diagram of the preparation and use of an x-ray scannable sliver that includes a sample in accordance with an example of the present application.
Figure 7:
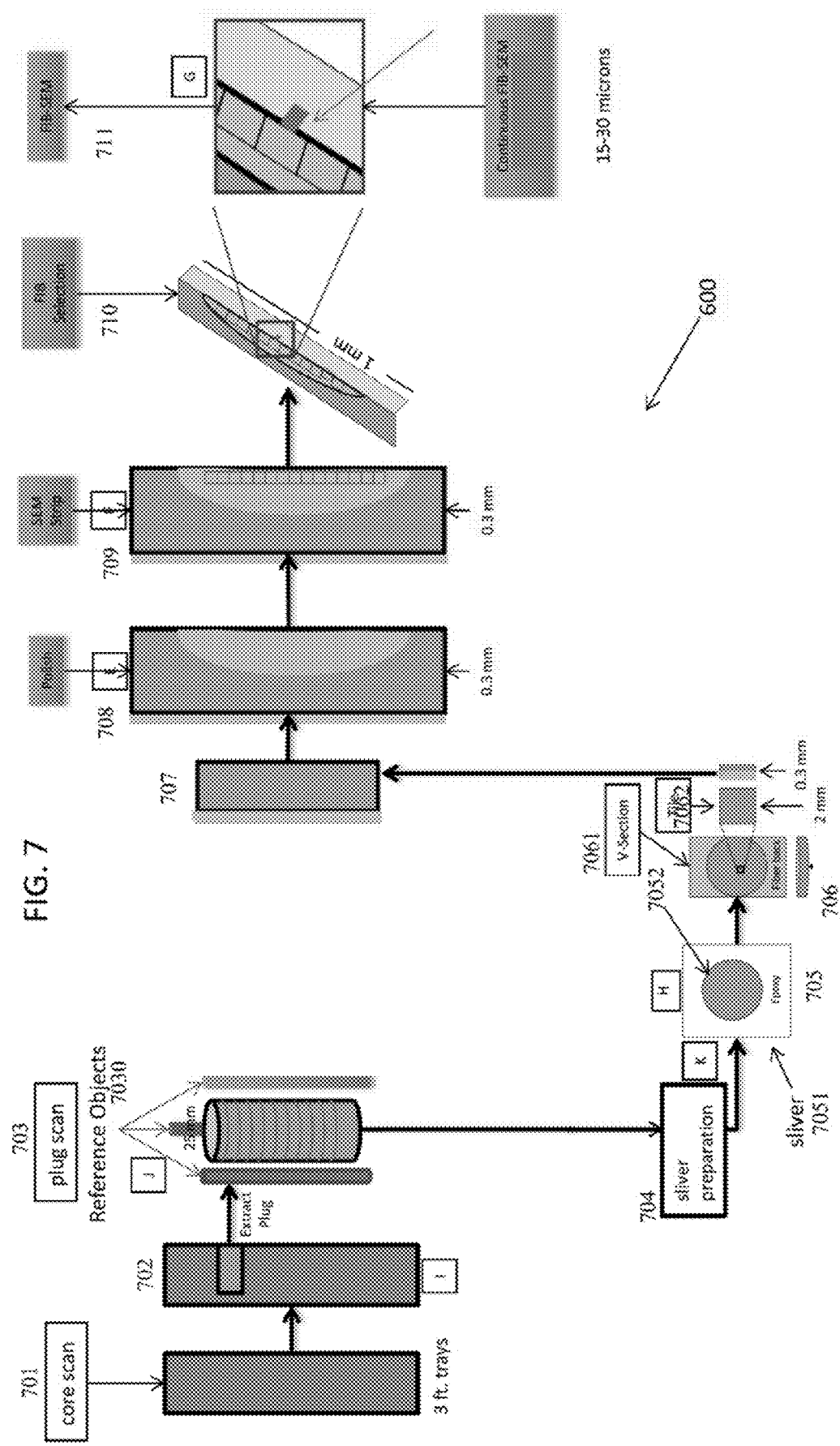
FIG. 7 shows a process flow diagram of the preparation and use of an x-ray scannable sliver that includes a sample and reference objects in accordance with an example of the present application.
Figure 8:
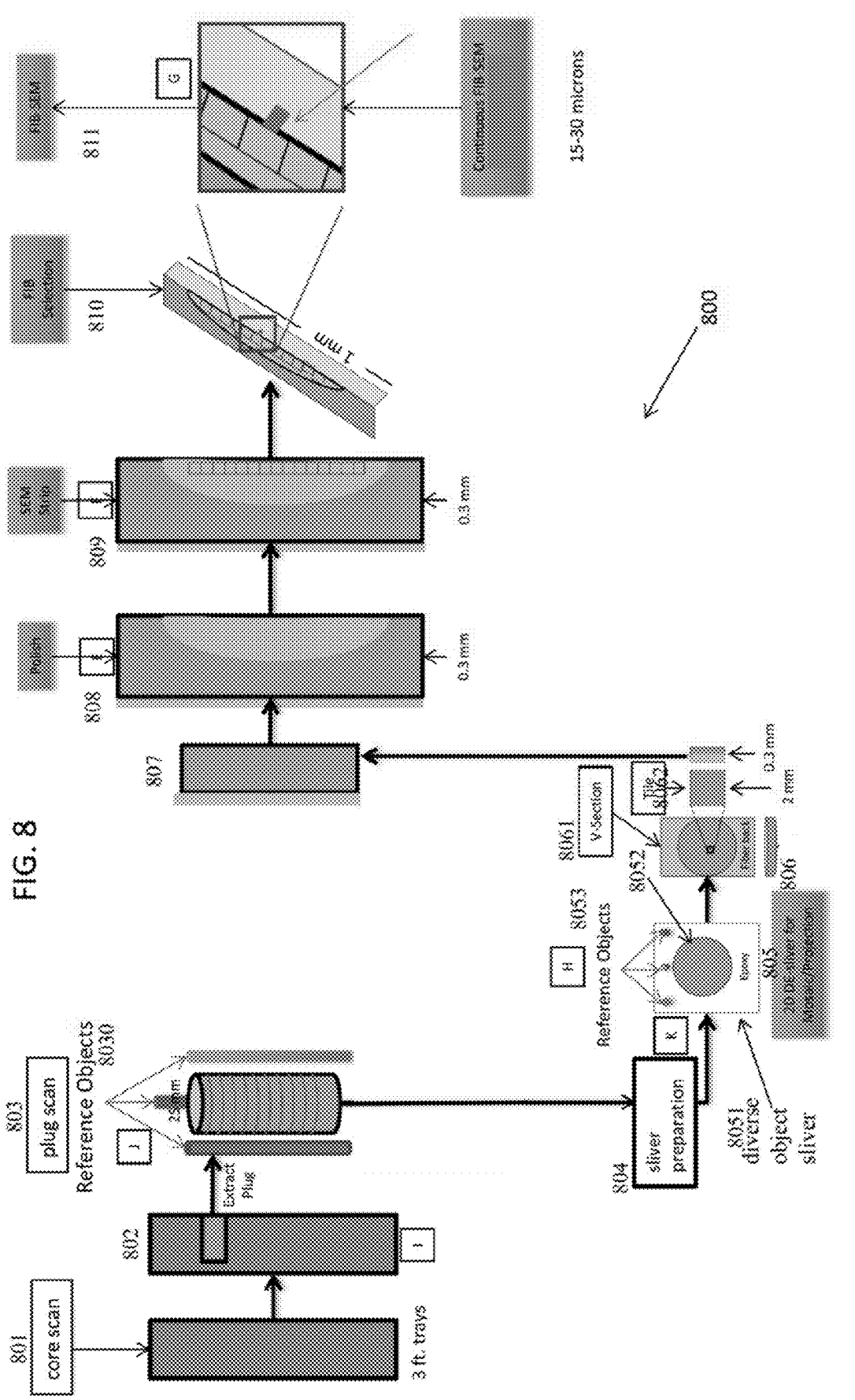
FIG. 8 shows a process flow diagram of the preparation and use of an x-ray scannable sliver that includes a sample and reference objects in accordance with an example of the present application.

FIGS. 6, 7, and 8 show additional examples of the present invention that provide for the preparation and use of an x-ray scannable sliver. In FIG. 6, the process flow 600 can include steps 601 (A), 602 (B), 603, 604, 605, 606, 607 (C), 608 (D), 609 (E), 610 (F), 611, and 612 (G) shown therein. Steps 601-604 and 607-612 can correspond to steps 101-103, 105, and 108-113, respectively, as shown and described for FIG. 1. Steps 605 and 606 can correspond to steps 404 and 405, respectively, as shown and described for FIG. 4. In step 606, the diverse object sliver 6061 includes a disc-shaped sample 6062 encased in encapsulant (e.g., polymer), and reference objects 6063. "V-section" 6071 and "Tile" 6072 can be similar to V-section 1081 and Tile 1082, respectively, in FIG. 1. In option 613 of this process flow, the extracted plug is single energy CT scanned before sample disc extraction and diverse sliver preparation, whereas in option 614 of this process flow this optional intermediate step is not used.

In FIG. 7, the process flow 700 can include steps 701, 702 (I), 703 (J), 704 (K), 705 (H), 706, 707, 708 (E), 709 (F), 710, and 711 (G) shown therein. Steps 701-703, and 707-711 can correspond to steps 401-403, and 408-412, respectively, as shown and described for FIG. 4. In step 703, for example, 3D dual energy CT scans can be performed on one or more plugs, such as up to 5 plugs or more, within the field of view (FOV), wherein a spacer sliver or slivers (e.g., glass slivers) can be positioned between plugs in a stack. Steps 704, 705, and 706 can correspond to steps 106, 107, and 108, respectively, as shown and described for FIG. 1. Reference objects 7030 shown in step 703 can be similar to reference objects 4030 of step 403 shown in FIG. 4. In step 705, the diverse object sliver 7051 includes a disc-shaped sample 7052. In step 706, data from the mosaic/projection scanning performed in step 705 is used for extraction of the sample selected in step 705. "V-section" 7061 and "Tile" 7062 can be similar to V-section 1081 and Tile 1082, respectively, in FIG. 1.

In FIG. 8 the process flow 800 can include steps 801, 802 (I), 803 (J), 804 (K), 805 (H), 806, 807, 808 (E), 809 (F), 810, and 811 (G) shown therein. Steps 801-811 can correspond to steps 401-405 and 407-412, respectively, as shown and described for FIG. 4. In step 803, for example, 3D dual energy CT scans can be performed on one or more plugs, such as up to 5 plugs or more, within the field of view (FOV), wherein a spacer sliver or slivers (e.g., glass slivers) can be positioned between plugs in a stack. Reference objects 8030 shown in step 803 can be similar to reference objects 4030 of step 403 shown in FIG. 4. In step 805, the diverse object sliver 8051 includes a disc-shaped sample 8052, and reference objects 8053. In step 806, data from the mosaic/projection scanning performed in step 805 is used for extraction of the sample selected in step 805. "V-section" 8061 and "Tile" 8062 can be similar to V-section 1081 and Tile 1082, respectively, in FIG. 1. Although not shown in FIG. 6, 7, or 8, a step of physical measurement of bulk density of the plug, such as described above for optional step 104 of the process in FIG. 1, can be included in any of these process flows prior to the sliver preparation step thereof Table 1 provides examples of different combinations of sample scanning procedures that can be used for plugs extracted at one depth interval in examples of the present application. The table shows combinations of various scanning procedure options including plugs scanned with or without external reference objects, plug CT scan energy (single or dual), sliver type with or without integral reference objects, and sliver projection scan energy (single or dual). Multi-energy scans that exceed the use of dual energy levels may be used where "dual-energy" is indicated in the table. As indicated, the list in Table 1 is for combinations for one depth interval, and the same types of combination options can be done for multiple depth intervals.

TABLE 1

| Plug Type - External Reference Objects | Plug CT Scan Energy | Sliver Type - Integral Reference Objects | Sliver Projection Scan Energy |
|---|---|---|---|
| Plug only | Single Energy | Sliver | Single Energy |
| Plug only | None | Sliver | Single Energy |
| Plug only | Single Energy | Sliver with integral reference objects | Dual Energy |
| Plug only | None | Sliver with integral reference objects | Dual Energy |
| Plug with external reference objects | Dual Energy | Sliver | Single Energy |
| Plug with external reference objects | Dual Energy | Sliver with integral reference objects | Dual Energy |

Figure 9:
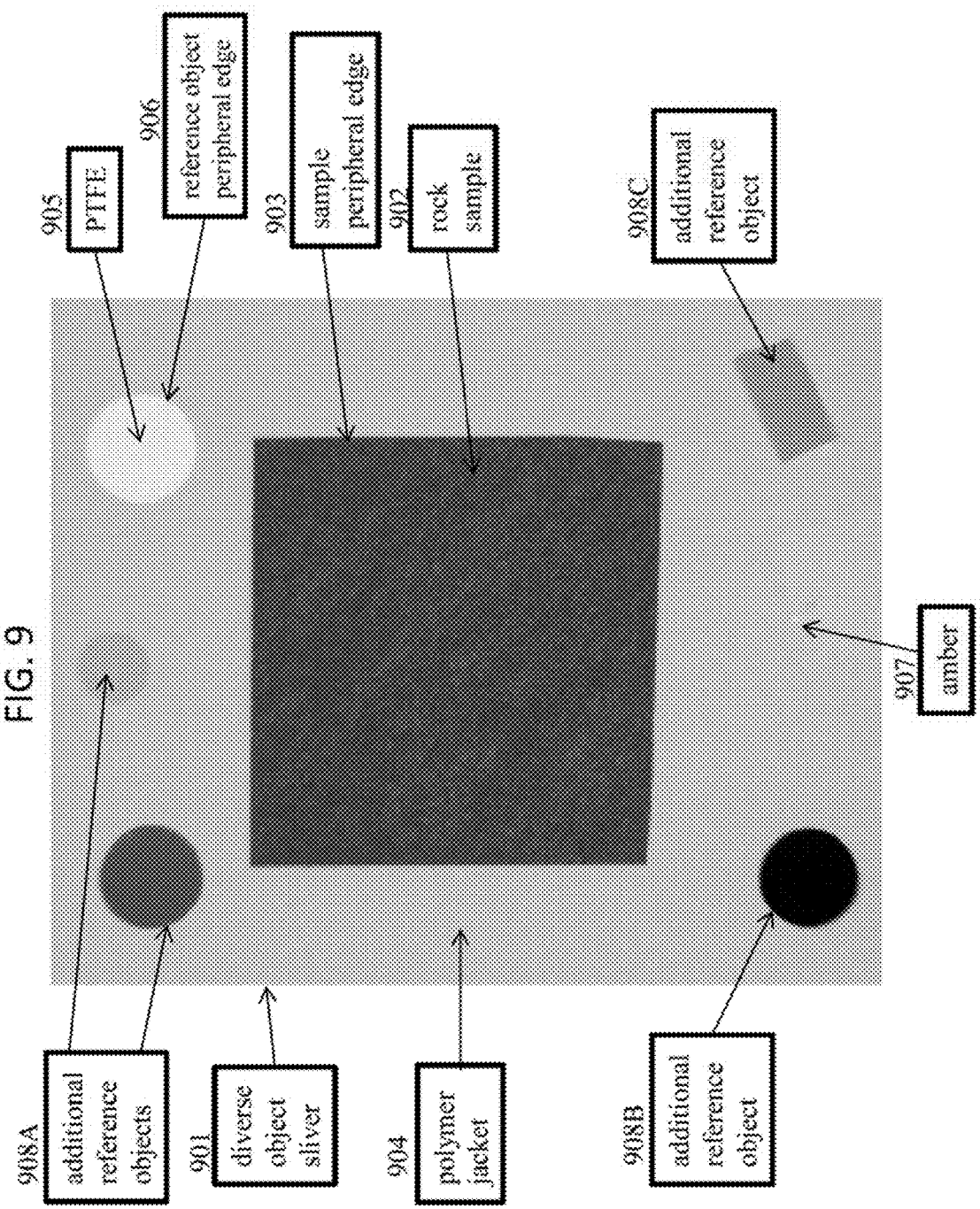
FIG. 9 is an enlarged image of a face of an x-ray scannable sliver that includes a thin discrete sample and thin discrete reference objects are encased around their peripheral edges with stabilization encapsulant (e.g., polymer) as a unitary discrete structure according to an example of the present application.

FIG. 9 shows an example of a diverse object sliver 901, such as prepared in step 404 of the process workflow 400 in FIG. 4, wherein the sliver 901 includes a rock sample 902 that is encased at its peripheral edge 903 by encapsulant (e.g., polymer) jacket 904. The sliver 901 also includes a plurality of reference objects 905 (PTFE (Teflon)), 907 (amber), 908A, 908B, and 908C, which also are encased along their respective peripheral edges, such as the indicated peripheral edge 906 of PTFE (Teflon) reference object 905, by the encapsulant (e.g., polymer) jacket 904. As the sliver 901 is unbacked, both sides or faces of the sliver can have the same layout and appearance of the sample, reference objects and encapsulant (e.g., polymer) jacket as mirror images of each other.

The method, system and unique workpieces of the present invention can allow for the accumulation of information about the attenuation during imaging that can be used for many qualitative and quantitative techniques. The present invention can have economic benefits such as wherein more imaging techniques (x-ray projection) can be utilized on samples prepared using these techniques. Also, the data created from these types of imaging can allow for more quantitative calculations to be performed. This method also can permit adjustment of digital rock analysis workflow that can allow for savings in time on x-ray projection and/or CT scanners. For example, more samples can be handled using a smaller number of x-ray scanners.

Figure 10:
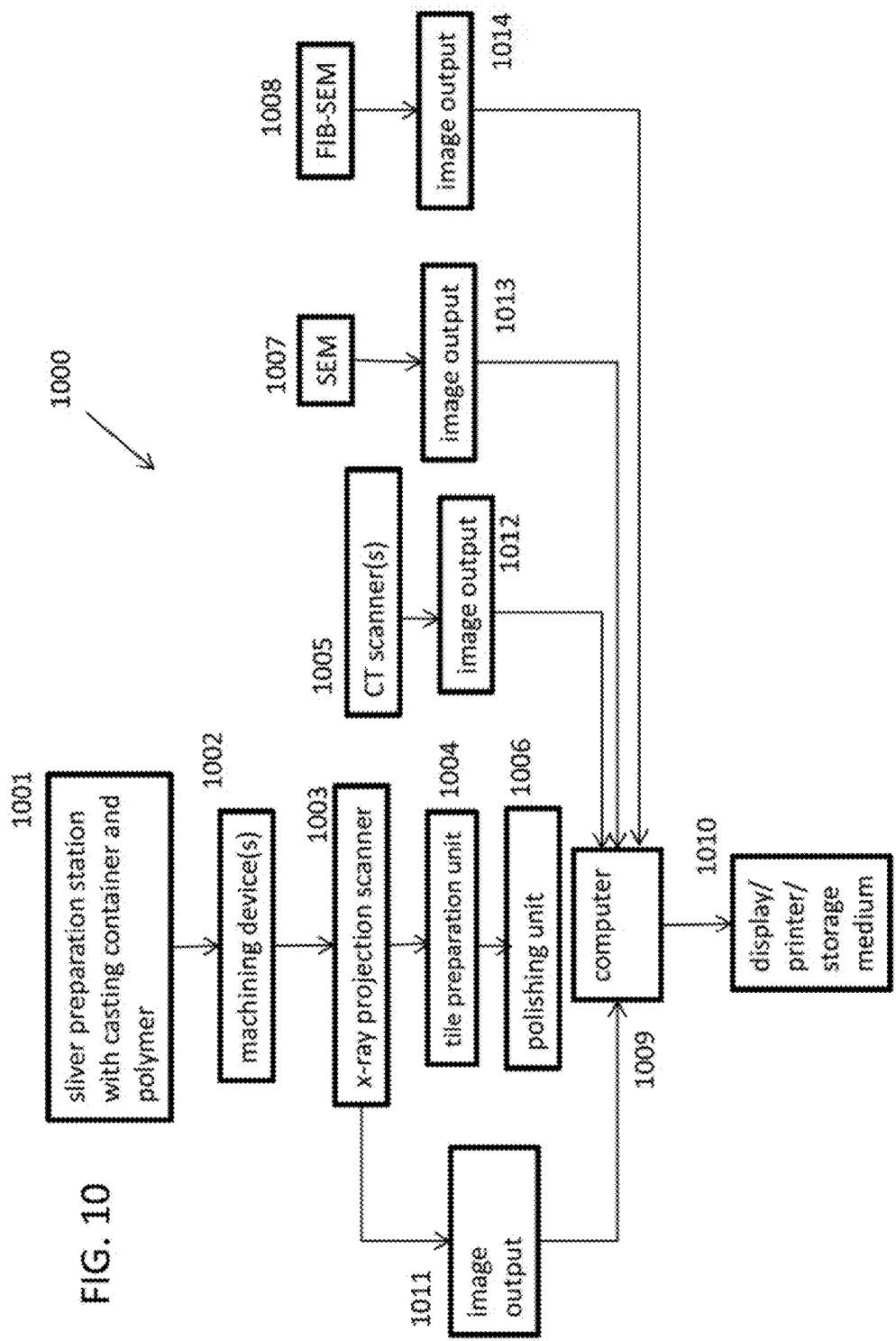
FIG. 10 is a system according to an example of the present application.

The present invention also relates to a system for preparing sample-embedded slivers for x-ray scanning and evaluation, such as according to the processes shown in FIGS. 1, 4, and 6-8. As illustrated in FIG. 10, for example, the system 1000 can include a sliver preparation station 1001 for positioning a sample and optionally reference objects in spaced apart locations within a casting container. As indicated, the sample and optional reference objects can be embedded in a hardened encapsulant (e.g., polymer) introduced into the container to provide a carrier that embeds the sample any reference objects. A machining device 1002 can be used for machining a side of the carrier to expose a flat first face, and the same or a different machining device can be used for machining an opposite side of the carrier to expose a flat second face to produce a sliver containing the sample with encapsulant (e.g., polymer) surrounding. As also indicated, an x-ray projection scanner 1003 can be included that has a stage capable of holding the sliver during scanning thereof As indicated, a tile can prepared with a selected area of the sliver sample for further processing with a backing layer, such as a carbon fiber backing layer and attachment adhesive, such as an epoxy, such as at a tile preparation unit or station 1004. As indicated, at least one single energy and/or multi-energy CT scanner 1005 optionally can be included in the system. As also indicated, a polishing unit or units 1006 for polishing a face of the sliver (e.g., mechanical and/or ion polishing units), an SEM 1007 for scanning the polished face of the sliver, and a FIB-SEM 1008 for scanning a selected portion of the polished face of the sliver, can be provided in the system. One or more computer systems 1009 can be provided for capture and processing of image data from the x-ray projection scanner 1003, the CT scanner or scanners 1005, the SEM 1007, and the FIB-SEM 1008, and to output the results to at least one output device 1010 to display, print, or store results of the computations. The computer system 1009 can be configured, for example, to receive image output 1011 from the x-ray projection scanner 1003, and also at least one or all of the image output 1012 from the CT scanner or scanners 1005, image output 1013 from the SEM 1007, and image output 1014 from the FIB-SEM 1008. The computer programs used for 2D and 3D image analysis and the computations can be stored, as a program product, on at least one non-transitory computer usable storage medium (e.g. a hard disk, a flash memory device, a compact disc, a magnetic tape/disk, or other media) associated with at least one processor (e.g., a CPU) which is adapted to run the programs, or may be stored on an external non-transitory computer usable storage medium which is accessible to the computer processor. The system of the present invention can be located and used off-site or on-site with respect to where the samples are obtained. If used off-site, samples can be transported to the location where the system is located. If used on-site, the system optionally can be used in a mobile enclosure such as a trailer, van, motor coach, or similar device, such that it can be transported to a well site or other sample source location and analyses run on-site.

The present invention includes the following aspects/embodiments/features in any order and/or in any combination:

1. A method for preparing a sample-embedded sliver for x-ray scanning and evaluation which comprises steps of:
   (i) extracting a plug from a core obtained from drilling a wellbore;
   (ii) optionally performing a single energy scan on the plug for sample selection;
   (iii) cutting a selected sample having opposite sides from the plug;
   (iv) positioning the sample within a casting container;
   (v) introducing flowable encapsulant (e.g., polymer) into the casting container to encapsulate at least a peripheral edge that extends around the sample and that is located between the opposite sides thereof;
   (vi) hardening the encapsulant (e.g., polymer) to form a sample-embedded intermediate carrier which is removable from the container;
   (vii) machining a side of the sample-embedded intermediate carrier to expose a flat face of the sample to produce a first exposed face; and
   (viii) machining to produce a second exposed face on an opposite side of the sample to the first exposed face, wherein the first and second faces are parallel to each other and spaced in part by a thickness of the sample, to provide an x-ray scannable discrete sliver comprising a thin planar sample encapsulated at a peripheral edge thereof within surrounding encapsulant (e.g., polymer) in thin layer form which structurally stabilizes the resulting sliver.
2. The method of any preceding or following embodiment/feature/aspect, further comprising measuring the bulk density of the core or plug before (iv).
3. The method of any preceding or following embodiment/feature/aspect, wherein the extracting (i) of the plug from the core comprises extracting a plug from a core and the extracted plug having a major length dimension that extends at substantially a right angle to a major length dimension of the core.
4. The method of any preceding or following embodiment/feature/aspect, wherein the cutting (iii) comprises cutting a thin disc from the plug to provide the sample, wherein the disc has opposite faces oriented substantially at right angles to the major length dimension of the plug.
5. The method of any preceding or following embodiment/feature/aspect, wherein (vii) machining comprises grinding a side of the sample-embedded carrier to expose a flat face of the sample to produce a first exposed face; and (viii) machining comprises cutting an exposed second face on an opposite side of the rock to the first exposed face.
6. The method of any preceding or following embodiment/feature/aspect, wherein the sample has a thickness of from about 1 to about 4 mm, and the sample in the sliver has a thickness of from about 0.5 to about 1.5 mm, wherein the thickness of the sample is greater than the thickness of the sample in the sliver.
7. The method of any preceding or following embodiment/feature/aspect, wherein the sample is rock.
8. The method of any preceding or following embodiment/feature/aspect, wherein the encapsulant (e.g., polymer) comprises curable epoxy.
9. The method of any preceding or following embodiment/feature/aspect, further comprising (ix) capturing a plurality of two-dimensional digital images of the sliver sample using x-ray projection scanning; and (x) selecting a sample area of the sliver sample in the plurality of two-dimensional digital images for further evaluation.
10. The method of any preceding or following embodiment/feature/aspect, wherein the selection of the sample area for further evaluation is made using visible indicia of x-ray attenuation as a variable from which interpretations for the selection are made.
11. The method of any preceding or following embodiment/feature/aspect, further comprising (xi) attaching the sliver to a backing layer, such as a carbon fiber backing, and (xii) cutting a tile portion from the sliver which includes the selected sample area.
12. The method of any preceding or following embodiment/feature/aspect, further comprising (xiii) ion polishing a face of the tile portion, (xiv) SEM scanning the polished face, (xv) selecting an area of the polished face for further evaluation using the SEM-scan results, and (xvi) FIB-SEM scanning the selected area in (xv).
13. The method of any preceding or following embodiment/feature/aspect, wherein the sample of the sliver is free of backing.
14. The present invention also relates to a method for preparing a sample-embedded sliver for x-ray scanning and evaluation which comprises steps of:
   (i) extracting a plurality of plugs from a core obtained from drilling a wellbore;
   (ii) machining the plurality of plugs to reduced thicknesses to provide samples;
   (iii) forming a stack of the samples with spacer slivers positioned between the samples;
   (iv) performing a multi-energy x-ray CT scan of the stack on a scanning stage at two or more different energy levels with a plurality of reference objects (e.g., 1, 2, 3, 4, 5, or more) placed around the samples on a scanning stage;
   (v) creating digital images of the samples from the multi-energy x-ray CT scan, wherein each of the samples scanned at two or more different energy levels returns for each energy a CT value for each voxel thereof;
   (vi) estimating bulk density, RhoB, and effective atomic number, $Z_{\mathit{eff}}$, per pixel for all the samples based on the digital images of the samples for sample selection;

(vii) positioning a selected sample and a plurality of discrete reference objects within a casting container;

(viii) introducing flowable encapsulant (e.g., polymer) into the casting container to encapsulate at least a peripheral edge that extends around the sample and between opposite sides thereof, and to encapsulate at least peripheral edges that extend around the reference objects and between opposite sides thereof;

(ix) hardening the encapsulant (e.g., polymer) to form a sample and reference object-embedded intermediate carrier which is removable from the container;

(x) machining a side of the sample and reference object-embedded intermediate carrier to expose a flat face of the sample and a flat face of each of the reference objects to produce a first exposed side; and (xi) machining to produce a second exposed side on an opposite side of the sample and reference objects to the first exposed side, wherein the first and second sides are parallel to each other and spaced in part by a thickness of the sample and thicknesses of the reference objects, to provide an x-ray scannable discrete sliver comprising a thin planar sample and reference objects encapsulated at respective peripheral edges thereof within surrounding encapsulant (e.g., polymer) in layer form, such as a thin layer form, which structurally stabilizes the resulting sliver.

15. The method of any preceding or following embodiment/feature/aspect, wherein the extracting (i) of the plugs from the core comprises extracting cylindrical plugs at differing depths along a side of the core having a larger cylindrical shape where bed boundary layers are substantially straight and uniform, and the extracted plugs each having a major length dimension that extends at substantially a right angle to a major length dimension of the core.

16. The method of any preceding or following embodiment/feature/aspect, wherein the machining of the extracted plugs forms discs having thicknesses of from about 4 mm to about 6 mm, wherein the discs has opposite faces oriented substantially at right angles to the major length dimension of the plugs.

17. The method of any preceding or following embodiment/feature/aspect, wherein the spacer slivers are glass.

18. The method of any preceding or following embodiment/feature/aspect, wherein the spacer slivers are glass slivers having a thickness of from about 0.5 mm to about 1.5 mm.

19. The method of any preceding or following embodiment/feature/aspect, wherein the plurality of discrete reference objects placed within the casting container comprise discrete pieces of quartz, polytetrafluoroethylene (PTFE), and amber.

20. The method of any preceding or following embodiment/feature/aspect, wherein the machining used to produce the first exposed side of samples and reference objects comprising grinding, and the machining used to produce the exposed second side of the samples and reference objects comprises cutting.

21. The method of any preceding or following embodiment/feature/aspect, wherein the sample in the sliver has a thickness of from about 0.5 to about 1.5 mm.

22. The method of any preceding or following embodiment/feature/aspect, wherein the reference objects in the sliver have the same thickness as the sample in the sliver.

23. The method of any preceding or following embodiment/feature/aspect, wherein the samples are rock.

24. The method of any preceding or following embodiment/feature/aspect, wherein the encapsulant (e.g., polymer) comprises curable epoxy.

25. The method of any preceding or following embodiment/feature/aspect, further comprising (xii) capturing a plurality of two-dimensional digital images of the sliver rock using x-ray projection scanning; and (xiii) selecting a sample area of the sliver rock in the plurality of two-dimensional digital images for further evaluation.

26. The method of any preceding or following embodiment/feature/aspect, further comprising (xiv) attaching the sliver to a carbon fiber backing, and (xv) cutting a tile portion from the sliver which includes the selected sample area.

27. The method of any preceding or following embodiment/feature/aspect, further comprising (xvi) ion polishing a face of the tile portion, (xvii) SEM scanning the polished face, (xviii) selecting an area of the polished face for further evaluation using the SEM-scan results, and (xix) FIB-SEM scanning the selected area in (xviii).

28. The present invention also relates to a system for preparing sample-embedded slivers for x-ray scanning and evaluation comprising:

(a) a preparation station comprising a sample and optionally reference objects positioned in spaced apart locations within a casting container, wherein the sample and optional reference objects are embedded in a hardened encapsulant (e.g., polymer) to provide a carrier, (b) a first machining device for machining a side of the carrier to expose a flat first face, (c) the first machining device or a second machining device for machining an opposite side of the carrier to expose a flat second face to produce a sliver containing the sample with encapsulant (e.g., polymer) surrounding, wherein the first and second faces are parallel to each other and spaced in part by a thickness of the sample and thicknesses of any reference objects, to provide an x-ray scannable discrete sliver comprising a thin planar sample and any reference objects encapsulated at respective peripheral edges thereof with surrounding encapsulant (e.g., polymer) in thin layer form which structurally stabilizes the resulting sliver.

(d) an x-ray scanner having a stage capable of holding the sliver during scanning thereof, (e) a tile preparation unit for attaching a selected area of the sliver sample to a backing with adhesive, (f) a polishing unit for polishing a face of the sliver, (g) an SEM for scanning the polished face of the sliver, (h) an FIB-SEM for scanning a selected portion of the polished face of the sliver, and (i) one or more computer systems operable to capture a plurality of two-dimensional digital images of the sliver rock using single or multi-energy x-ray scanning, and to output the results to at least one device to display, print, or store results of the computations.

29. The present invention also relates to an x-ray scannable sliver comprising a thin discrete sample and a plurality of thin discrete reference objects encapsulated by hardened encapsulant (e.g., polymer) that surrounds the peripheral edges of the sample and reference objects.

30. The x-ray scannable sliver of any preceding or following embodiment/feature/aspect, wherein the hardened encapsulant (e.g., polymer) comprises cured epoxy and the plurality of reference objects comprises three or more reference objects which have a different effective atomic number and/or bulk density from each other.

31. The x-ray scannable sliver of any preceding or following embodiment/feature/aspect, wherein the reference objects are quartz, polytetrafluoroethylene (PTFE), and amber.

32. The x-ray scannable sliver of any preceding or following embodiment/feature/aspect, wherein the sample of the sliver is free of backing.

33. The present invention also relates to a method for preparing a sample-embedded sliver for x-ray scanning and evaluation which comprises steps of:
(i) obtaining a cut sample from a plug;
(ii) encapsulating the cut sample to encapsulate at least a peripheral edge that extends around the sample and that is located between the opposite sides thereof;
(iii) exposing, if not exposed already, a flat face of the cut sample to produce a first exposed face; and
(iv) exposing, if not exposed already, a second exposed face on an opposite side of the cut sample to the first exposed face, wherein the first and second faces are parallel to each other and spaced in part by a thickness of the sample, to provide an energy, scannable sliver.

34. The present invention also relates to a method for preparing and utilizing a sample-embedded sliver for x-ray scanning and evaluation which comprises steps of:
(i) extracting a plug from a core obtained from drilling a wellbore;
(ii) optionally performing a single energy scan on the plug for sample selection;
(iii) cutting a selected sample having opposite sides from the plug;
(iv) positioning the sample within a casting container;
(v) introducing flowable encapsulant (e.g., polymer) into the casting container to encapsulate at least a peripheral edge that extends around the sample and that is located between the opposite sides thereof;
(vi) hardening the encapsulant (e.g., polymer) to form a sample-embedded intermediate carrier which is removable from the container;
(vii) machining a side of the sample-embedded intermediate carrier to expose a flat face of the sample to produce a first exposed face;
(viii) machining to produce a second exposed face on an opposite side of the sample to the first exposed face, wherein the first and second faces are parallel to each other and spaced in part by a thickness of the sample, to provide an x-ray scannable discrete sliver comprising a thin planar sliver sample encapsulated at a peripheral edge thereof within surrounding encapsulant (e.g., polymer) in thin layer form which structurally stabilizes the resulting sliver; and
(ix) capturing at least one digital image of the sliver sample using x-ray scanning.

35. The present invention also relates to a method for preparing and utilizing a sample-embedded sliver for x-ray scanning and evaluation which comprises steps of:
(i) extracting a plurality of plugs from a core obtained from drilling a wellbore;
(ii) machining the plurality of plugs to reduced thicknesses to provide samples;
(iii) forming a stack of the samples with spacer slivers positioned between the samples;
(iv) performing a multi-energy x-ray CT scan of the stack on a scanning stage at two or more different energy levels with a plurality of reference objects placed around the samples on a scanning stage;
(v) creating digital images of the samples from the multi-energy x-ray CT scan, wherein each of the samples scanned at two or more different energy levels returns for each energy a CT value for each voxel thereof;
(vi) estimating bulk density, RhoB, and effective atomic number, $Z_{eff}$, per pixel for all the samples based on the digital images of the samples for sample selection;
(vii) positioning a selected sample and a plurality of discrete reference objects within a casting container;
(viii) introducing flowable encapsulant (e.g., polymer) into the casting container to encapsulate at least a peripheral edge that extends around the sample and between opposite sides thereof, and to encapsulate at least peripheral edges that extend around the reference objects and between opposite sides thereof;
(ix) hardening the encapsulant (e.g., polymer) to form a sample and reference object-embedded intermediate carrier which is removable from the container;
(x) machining a side of the sample and reference object-embedded intermediate carrier to expose a flat face of the sample and a flat face of each of the reference objects to produce a first exposed side;
(xi) machining to produce a second exposed side on an opposite side of the sample and reference objects to the first exposed side, wherein the first and second sides are parallel to each other and spaced in part by a thickness of the sample and thicknesses of the reference objects, to provide an x-ray scannable discrete sliver comprising a thin planar sliver sample and reference objects encapsulated at respective peripheral edges thereof within surrounding encapsulant (e.g., polymer) in thin layer form which structurally stabilizes the resulting sliver; and
(xii) capturing at least one digital image of the sliver sample using x-ray scanning.

36. The present invention also relates to a method for preparing and utilizing a sample-embedded sliver for x-ray scanning and evaluation which comprises steps of:
(i) obtaining a cut sample from a plug;
(ii) encapsulating the cut sample to encapsulate at least a peripheral edge that extends around the sample and that is located between the opposite sides thereof;
(iii) exposing, if not exposed already, a flat face of the cut sample to produce a first exposed face;
(iv) exposing, if not exposed already, a second exposed face on an opposite side of the cut sample to the first exposed face, wherein the first and second faces are parallel to each other and spaced in part by a thickness of the sample, to provide an energy scannable sliver comprising a sliver sample; and
(v) capturing at least one digital image of the sliver sample using x-ray scanning.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for preparing and utilizing a sample-embedded sliver for x-ray scanning and evaluation which comprises steps of:
(i) extracting a plug from a core obtained from drilling a wellbore;
(ii) optionally performing a single energy scan on the plug for sample selection;
(iii) cutting a selected sample having opposite sides from the plug;
(iv) positioning the sample within a casting container;
(v) introducing flowable encapsulant into the casting container to encapsulate at least a peripheral edge that extends around the sample and between the opposite sides thereof;
(vi) hardening the encapsulant to form a sample-embedded intermediate carrier which is removable from the container;
(vii) machining a side of the sample-embedded intermediate carrier to expose a flat face of the sample to produce a first exposed face;
(viii) machining to produce a second exposed face on an opposite side of the sample to the first exposed face, wherein the first and second faces are parallel to each other and spaced in part by a thickness of the sample, to provide an x-ray scannable discrete sliver comprising a thin planar sliver sample encapsulated at a peripheral edge thereof within surrounding encapsulant in thin layer form which structurally stabilizes the resulting sliver; and
(ix) capturing at least one digital image of the sliver sample using x-ray scanning.

2. The method of claim 1, further comprising measuring the bulk density of the core or plug before (iv).

3. The method of claim 1, wherein the extracting (i) of the plug from the core comprises extracting a plug from a core and the extracted plug having a major length dimension that extends at substantially a right angle to a major length dimension of the core.

4. The method of claim 3, wherein the cutting (iii) comprises cutting a thin disc from the plug to provide the sample, wherein the disc has opposite faces oriented substantially at right angles to the major length dimension of the plug.

5. The method of claim 1, wherein (vii) machining comprises grinding a side of the sample-embedded carrier to expose a flat face of the sample to produce a first exposed face; and (viii) machining comprises cutting an exposed second face on an opposite side of the rock to the first exposed face.

6. The method of claim 1, wherein the sample has a thickness of from about 1 to about 4 mm, and the sample in the sliver has a thickness of from about 0.5 to about 1.5 mm, wherein the thickness of the sample is greater than the thickness of the sample in the sliver.

7. The method of claim 1, wherein the sample is rock.

8. The method of claim 1, wherein the encapsulant comprises curable epoxy.

9. The method of claim 1, further comprising (ix) capturing a plurality of two-dimensional digital images of the sliver sample using x-ray projection scanning; and (x) selecting a sample area of the sliver sample in the plurality of two-dimensional digital images for further evaluation.

10. The method of claim 9, wherein the selection of the sample area for further evaluation is made using visible indicia of x-ray attenuation as a variable from which interpretations for the selection are made.

11. The method of claim 10, further comprising (xi) attaching the sliver to a backing, and (xii) cutting a tile portion from the sliver which includes the selected sample area.

12. The method of claim 11, further comprising (xiii) ion polishing a face of the tile portion, (xiv) SEM scanning the polished face, (xv) selecting an area of the polished face for further evaluation using the SEM-scan results, and (xvi) FIB-SEM scanning the selected area in (xv).

13. The method of claim 1, wherein the sample of the sliver is free of backing.

14. A method for preparing and utilizing a sample-embedded sliver for x-ray scanning and evaluation which comprises steps of:
(i) extracting a plurality of plugs from a core obtained from drilling a wellbore;
(ii) machining the plurality of plugs to reduced thicknesses to provide samples;
(iii) forming a stack of the samples with spacer slivers positioned between the samples;
(iv) performing a multi-energy x-ray CT scan of the stack on a scanning stage at two or more different energy levels with a plurality of reference objects placed around the samples on a scanning stage;
(v) creating digital images of the samples from the multi-energy x-ray CT scan, wherein each of the samples scanned at two or more different energy levels returns for each energy a CT value for each voxel thereof;
(vi) estimating bulk density, RhoB, and effective atomic number, $Z_{eff}$, per pixel for all the samples based on the digital images of the samples for sample selection;
(vii) positioning a selected sample and a plurality of discrete reference objects within a casting container;
(viii) introducing flowable encapsulant into the casting container to encapsulate at least a peripheral edge that extends around the sample and between opposite sides thereof, and to encapsulate at least peripheral edges that extend around the reference objects and between opposite sides thereof;
(ix) hardening the encapsulant to form a sample and reference object-embedded intermediate carrier which is removable from the container;
(x) machining a side of the sample and reference object-embedded intermediate carrier to expose a flat face of the sample and a flat face of each of the reference objects to produce a first exposed side;
(xi) machining to produce a second exposed side on an opposite side of the sample and reference objects to the first exposed side, wherein the first and second sides are parallel to each other and spaced in part by a thickness of the sample and thicknesses of the reference objects, to provide an x-ray scannable discrete sliver comprising a thin planar sliver sample and reference objects encapsulated at respective peripheral edges thereof within surrounding encapsulant in thin layer form which structurally stabilizes the resulting sliver; and
(xii) capturing at least one digital image of the sliver sample using x-ray scanning.

15. The method of claim 14, wherein the extracting (i) of the plugs from the core comprises extracting cylindrical plugs at differing depths along a side of the core having a larger cylindrical shape where bed boundary layers are substantially straight and uniform, and the extracted plugs each having a major length dimension that extends at substantially a right angle to a major length dimension of the core.

16. The method of claim 14, wherein the machining of the extracted plugs forms discs having thicknesses of from about 4 mm to about 6 mm, wherein the discs has opposite faces oriented substantially at right angles to the major length dimension of the plugs.

17. The method of claim 16, wherein the spacer slivers are glass.

18. The method of claim 16, wherein the spacer slivers are glass slivers having a thickness of from about 0 5 mm to about 1.5 mm.

19. The method of claim 14, wherein the plurality of discrete reference objects placed within the casting container comprise discrete pieces of quartz, polytetrafluoroethylene (PTFE), and amber.

20. The method of claim 14, wherein the machining used to produce the first exposed side of samples and reference objects comprising grinding, and the machining used to produce the exposed second side of the samples and reference objects comprises cutting.

21. The method of claim 14, wherein the sample in the sliver has a thickness of from about 0.5 to about 1.5 mm.

22. The method of claim 21, wherein the reference objects in the sliver have the same thickness as the sample in the sliver.

23. The method of claim 14, wherein the samples are rock.

24. The method of claim 14, wherein the encapsulant comprises curable epoxy.

25. The method of claim 14, wherein (xii) comprises capturing a plurality of two-dimensional digital images of the sliver sample using x-ray projection scanning; and further comprising (xiii) selecting a sample area of the sliver sample in the plurality of two-dimensional digital images for further evaluation.

26. The method of claim 25, further comprising (xiv) attaching the sliver to a backing, and (xv) cutting a tile portion from the sliver which includes the selected sample area.

27. The method of claim 26, further comprising (xvi) ion polishing a face of the tile portion, (xvii) SEM scanning the polished face, (xviii) selecting an area of the polished face for further evaluation using the SEM-scan results, and (xix) FIB-SEM scanning the selected area in (xviii).

28. A system for preparing sample-embedded slivers for x-ray scanning and evaluation comprising:
  (a) a preparation station comprising a sample and optionally reference objects positioned in spaced apart locations within a casting container, wherein the sample and optional reference objects are embedded in a hardened encapsulant to provide a carrier,
  (b) a first machining device for machining a side of the carrier to expose a flat first face,
  (c) the first machining device or a second machining device for machining an opposite side of the carrier to expose a flat second face to produce a sliver containing the sample with encapsulant surrounding, wherein the first and second faces are parallel to each other and spaced in part by a thickness of the sample and thicknesses of any reference objects, to provide an x-ray scannable discrete sliver comprising a thin planar sample and any reference objects encapsulated at respective peripheral edges thereof with surrounding encapsulant in thin layer form which structurally stabilizes the resulting sliver.
  (d) an x-ray scanner having a stage capable of holding the sliver during scanning thereof,
  (e) a tile preparation unit for attaching a selected area of the sliver sample to a backing with adhesive,
  (f) a polishing unit for polishing a face of the sliver,
  (g) an SEM for scanning the polished face of the sliver,
  (h) an FIB-SEM for scanning a selected portion of the polished face of the sliver, and
  (i) one or more computer systems operable to capture a plurality of two-dimensional digital images of the sliver rock using single or multi-energy x-ray scanning, and to output the results to at least one device to display, print, or store results of the computations.

29. An x-ray scannable sliver comprising a thin discrete sample and a plurality of thin discrete reference objects encapsulated by hardened encapsulant that surrounds the peripheral edges of the sample and reference objects.

30. The x-ray scannable sliver of claim 29, wherein the hardened encapsulant comprises cured epoxy and the plurality of reference objects comprises three or more reference objects which have a different effective atomic number and/or bulk density from each other.

31. The x-ray scannable sliver of claim 30, wherein the reference objects are quartz, polytetrafluoroethylene (PTFE), and amber.

32. The x-ray scannable sliver of claim 29, wherein the sample of the sliver is free of backing.

33. A method for preparing and utilizing a sample-embedded sliver for x-ray scanning and evaluation which comprises steps of:
  (i) obtaining a cut sample from a plug;
  (ii) encapsulating the cut sample to encapsulate at least a peripheral edge that extends around the sample and that is located between the opposite sides thereof;
  (iii) exposing, if not exposed already, a flat face of the cut sample to produce a first exposed face;
  (iv) exposing, if not exposed already, a second exposed face on an opposite side of the cut sample to the first exposed face, wherein the first and second faces are parallel to each other and spaced in part by a thickness of the sample, to provide an energy scannable sliver comprising a sliver sample; and
  (v) capturing at least one digital image of the sliver sample using x-ray scanning.

* * * * *